(12) United States Patent
Gehrlein et al.

(10) Patent No.: US 7,057,722 B2
(45) Date of Patent: Jun. 6, 2006

(54) METHOD AND APPARATUS FOR DETERMINING THE HOMOGENEITY OF A GRANULATION DURING TABLETING

(75) Inventors: Lane Gehrlein, Pine Island, NY (US); Emil Ciurczak, Goldens Bridge, NY (US); Gary Ritchie, Kent, CT (US); Kevin C. Bynum, Yonkers, NY (US)

(73) Assignee: Euro-Celtique S.A., Luxembourg (LU)

( * ) Notice: Subject to any disclaimer, the term of this patent is extended or adjusted under 35 U.S.C. 154(b) by 284 days.

(21) Appl. No.: 10/406,737

(22) Filed: Apr. 3, 2003

(65) Prior Publication Data

US 2004/0012781 A1  Jan. 22, 2004

Related U.S. Application Data

(60) Provisional application No. 60/369,823, filed on Apr. 4, 2002.

(51) Int. Cl.
*G01J 3/28* (2006.01)
*B01F 9/00* (2006.01)

(52) U.S. Cl. .................. 356/328; 356/419; 366/142; 366/143

(58) Field of Classification Search ................ 356/326, 356/328, 72, 419; 366/142, 143
See application file for complete search history.

(56) References Cited

U.S. PATENT DOCUMENTS

| | | | |
|---|---|---|---|
| 3,416,864 A | 12/1968 | Keahl et al. | 356/100 |
| 4,054,389 A | 10/1977 | Owen | 356/189 |
| 5,504,332 A | 4/1996 | Richmond et al. | 250/339.12 |
| 5,582,644 A | 12/1996 | Gaddis et al. | 118/303 |
| 5,653,940 A | 8/1997 | Carey et al. | 422/52 |
| 5,859,708 A | 1/1999 | Feldman | 356/406 |
| 5,927,558 A | 7/1999 | Bruce | 222/185.1 |
| 5,946,088 A | 8/1999 | Aldridge | 356/300 |
| 6,057,514 A | 5/2000 | Maguire | 177/105 |
| 6,517,230 B1 | 2/2003 | Afnan et al. | 366/142 |

FOREIGN PATENT DOCUMENTS

| WO | 0160503 | 8/2001 |
|---|---|---|
| WO | WO 02/18912 | * 3/2002 |

* cited by examiner

*Primary Examiner*—F. L. Evans
(74) *Attorney, Agent, or Firm*—Davidson, Davidson & Kappel, LLC

(57) ABSTRACT

An apparatus for detecting the homogeneity of a pharmaceutical mixture has a hopper for containing a mixture of two or more pharmaceutical components and that is situated within a production line of preparation of a pharmaceutical dosage form. A spectroscope is mounted to the hopper for measuring spectroscopic characteristics of the mixture, and a processing device that is not physically coupled to the spectroscope analyzes the spectroscopic characteristics of the mixture and derives information regarding the homogeneity of the mixture. The spectroscope wirelessly sends the spectroscopic characteristics to the processing device, which derives information regarding the homogeneity of the mixture. The wireless transmission of the spectroscopic characteristics can be done through infrared radiation or near infrared radiation, and the spectroscopic characteristics can be converted to digital signals prior to being transmitted.

77 Claims, 29 Drawing Sheets

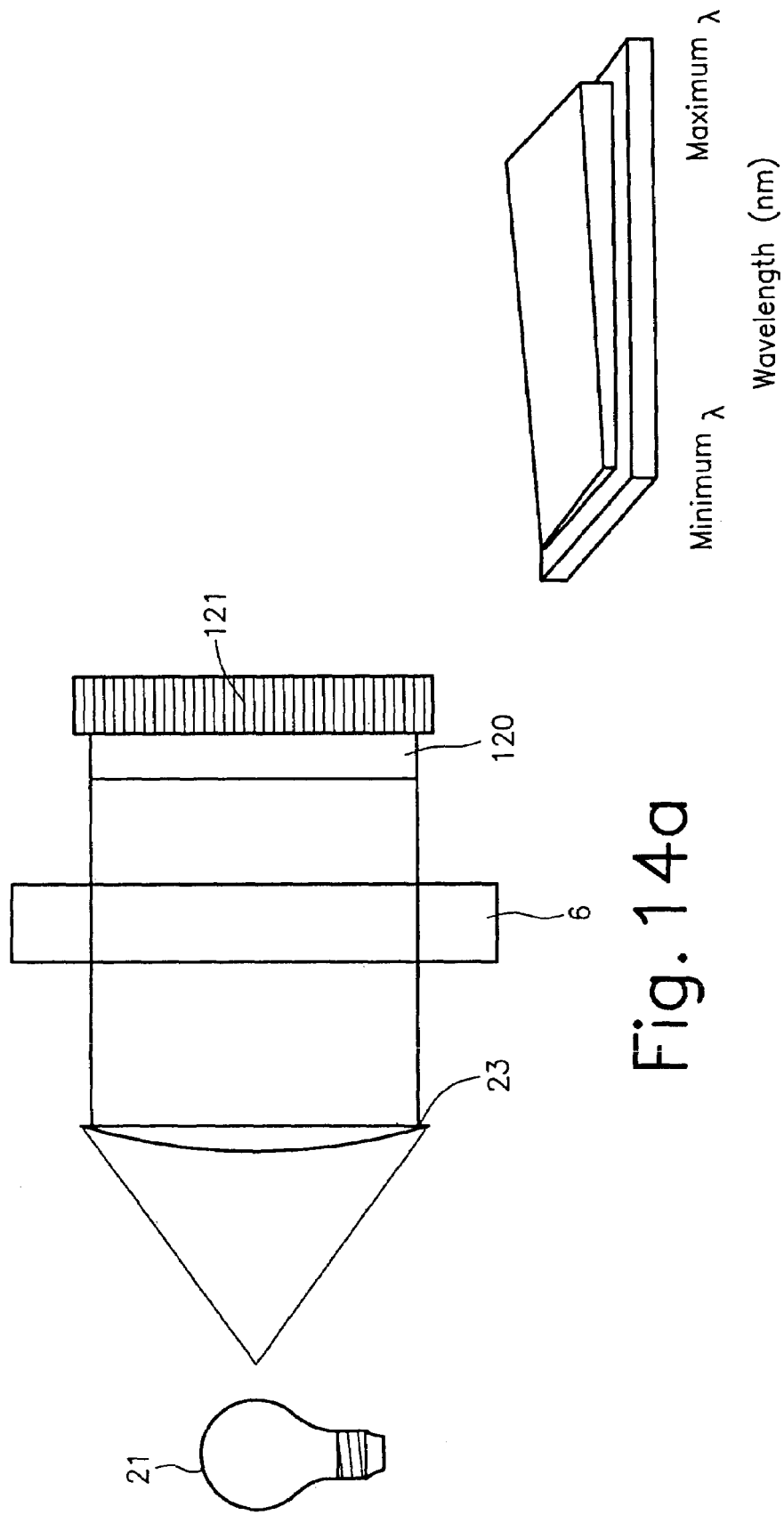

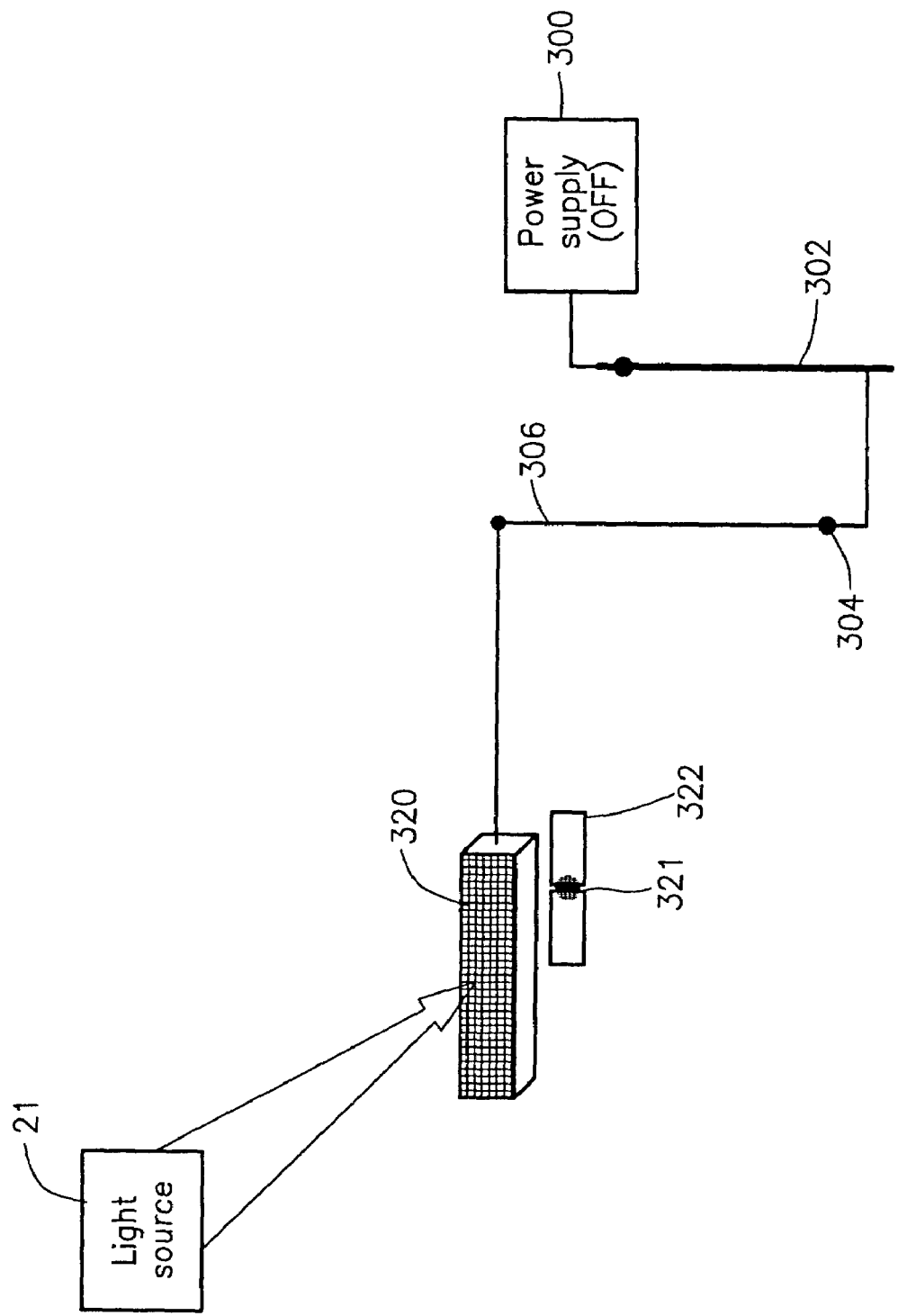

METHOD AND APPARATUS FOR DETERMINING THE HOMOGENEITY OF A GRANULATION DURING TABLETING

This application claims priority from U.S. Provisional Application No. 60/369,823 filed on Apr. 4, 2002, the entire disclosure of which is hereby incorporated by reference.

FIELD OF THE INVENTION

The present invention relates generally to the detection of the homogeneity of a mixture of components.

BACKGROUND OF THE INVENTION

Pharmaceutical raw materials may be plant, animal or other biological products; inorganic elements and compounds; or organic compounds. If the raw material is the subject of a monograph in a pharmacopoeia or national formulary, a minimum acceptable degree of chemical purity is specified in order to ensure consumer safety. Pharmaceutical compositions, which usually include any number of separate components, including the active drug, are typically mixed into a homogeneous mixture. Public safety requires assurance of accuracy in dosages of pharmaceutical medication, and any blending operation of pharmaceutical raw materials generally seeks to achieve complete uniformity and homogeneity.

A hopper may be used to feed pharmaceutical raw material into a mixing device, such as a blender, where the drug is mixed with other ingredients, generally non-pharmaceutically-active components known as excipients, in order to form a dosage form such as a tablet or capsule. During this process, the drug is mixed with suitable excipients such as dextrin, lactose, salt, polymers, celluloses, stearic acid, talc, or other inactive ingredients. The dosage unit can then be packaged as is, or it may be further modified into a more convenient form for administration to a patient, such as a capsule or tablet.

A tableting or encapsulating machine may be used to form the capsule or tablet dosage form. Hoppers can also be used to feed the pharmaceutical raw material (which may be in the form of a granulate or dry blend) into a tableting/encapsulating machine.

However, vibrations that occur during the manufacturing process may cause stratification of the granules within the hopper prior to preparation of the dosage form. Stratification is localized areas of differing drug potencies, and may occur even though the composition within a localized area is itself homogeneous. Stratification may be related to, varying particle size. A consequence of stratification may be a dosage form being prepared with an inaccurate dosage (e.g., a sub-potent or a super-potent product). Accordingly, the mixing of pharmaceutical compositions is a crucial step in processing an active drug into a dosage form.

Generally, the homogeneity of a pharmaceutical composition refers to the distribution of the active drug in the pharmaceutical composition, and the potency of a pharmaceutical composition refers to the amount of the active component in the pharmaceutical composition. Traditionally, the determinations of the homogeneity and potency of a pharmaceutical mixture have been time consuming. In addition, traditional methods measure the homogeneity and potency only of the active component in a pharmaceutical composition and give no information concerning the homogeneity of the non-active components.

It is also important to determine the concentration of the other, non-active components within the pharmaceutical mixture. The concentration of the non-active components in a pharmaceutical mixture is important because it determines the physical properties of the mixture. For example, disintegrants affect the rate of dissolution of a tablet in a recipient's stomach. If the disintegrant is not homogeneously distributed in the pharmaceutical mixture, then the resulting tablets may not dissolve at a uniform rate, thereby potentially resulting in quality, dosing and bioavailability problems. Thus, it is important to measure the homogeneity of all the components of a pharmaceutical mixture because the dispersion of certain components may ultimately affect the physical properties of the final form of the pharmaceutical composition.

Additionally, as noted above, stratification my be associated with uneven distribution of particle size. The result may be quality, dosing and bioavailability problems.

One method of determining the homogeneity and potency of a pharmaceutical mixture involves removing samples of the mixture from various locations along the path of preparation of the pharmaceutical mixture, such as the hoppers and blender, and analyzing these samples for homogeneity and potency. In doing so, a technician must first stop the process, remove samples of the composition mixture and assay those samples in a laboratory. The samples are typically analyzed using a technique such as ultra-violet (UV) spectroscopy or High Performance Liquid Chromatography (HPLC) to determine whether the active pharmaceutical component is uniformly dispersed (is homogeneous) in the mixture and present at an appropriate concentration level. This information reflects the potency of the mixture, and, if the potency of each sample is the same, then the mixture is considered to be homogeneous. However, neither UV nor HPLC analysis establishes the concentration of the non-active components of the mixture. Furthermore, while the samples are taken to the laboratory and analyzed, the blending or dosage formulation process must be put on hold.

Alternatively, infrared spectroscopy, which can be useful in measuring the molecular composition of pharmaceuticals, can also be used to determine the homogeneity and potency of the ingredients of a pharmaceutical mixture. Infrared radiation (IR) may be roughly divided into three wavelength bands: near-infrared radiation, mid-infrared radiation, and far-infrared radiation. Near-infrared radiation (NIR) is radiation having a wavelength between about 750 nm and about 3000 nm. Mid-infrared radiation (MIR) is radiation having a wavelength, between about 3000 nm and about 10,000 nm. Far-infrared radiation (FIR) is radiation having a wavelength between about 10,000 nm and about 1000 μm (1000 μm being the beginning of the microwave region). The desired range may be chosen to suit the analysis being performed.

In general spectrometers (e.g., spectrophotometers) can be divided into two classes: transmittance spectrometers and reflectance spectrometers. In a transmittance spectrometer, light is directed onto a sample, and a detector detects the light which was transmitted through the sample. In contrast, in a reflectance spectrometer, light is directed onto a sample and one or more detectors detect the light which was reflected from the sample. Depending upon its design, a spectrometer may, or may not, be used as both a transmittance and a reflectance spectrometer.

One method of determining the homogeneity and potency of the components of a pharmaceutical mixture using infrared spectrometry is shown in U.S. Pat. No. 5,504,332 to Richmond et al., which purports to disclose a system that uses near infrared technology for analyzing the uniformity and mass balance of the pharmaceutical mixture in order to control the tablet manufacturing process. The system has a library consisting of near infrared spectral scan data of pharmaceutical materials spanning the normal process range. The patent states that the assessment of uniformity of a sample mixture is accomplished by comparison of near infrared spectral information regarding the sample with the library of near infrared spectral scans of acceptable material. However, the pharmaceutical material is not subjected to near infrared analysis while the pharmaceutical material is being manufactured. Rather, it is analyzed in a separate device, e.g, as a tablet or as a sample.

Another method of determining the homogeneity and potency of the components of a pharmaceutical mixture using infrared spectrometry, although only during active mixing within a blender, is shown in U.S. Pat. No. 5,946,088 to Aldridge, which purports to disclose an apparatus for detecting the homogeneity and potency of a mixture of compositions of matter during the mixing process using a spectrometer. The described apparatus has a V-shaped container that rotates about a horizontal axis of rotation during the mixing process, and the wall of the container includes a single aperture at the location in the wall intersecting the axis of rotation of the container. The patent describes that a radiation detector for detecting spectroscopic characteristics of the mixture is rotatably mounted through the inside of a hollow shaft about which the container rotates, and connections to a remote spectroscopic means and computer, including a fiber optic bundle, are made through the rotational shaft. The computer synchronizes the taking of spectroscopic data by the detector with a predetermined single rotational position or multiple rotational positions of the container, as the taking of spectral data at a consistent predetermined point in the rotation of the container, according to this patent, assures a greater degree of accuracy in determining the homogeneity of the mixture being mixed.

SUMMARY OF THE INVENTION

Prior art devices use infrared spectrometers that transmit their data measurements of the molecular composition of pharmaceuticals by a physical connection, rather than by a wireless one. Thus, such spectrometers remain physically connected to devices that interpret the data and to devices that contain the pharmaceutical mixtures. The necessity of such a physical connection increases the number of devices necessary to analyze the spectral data and increases the complexity of the device that prepares the pharmaceutical dosage form.

In wireless transmissions of data, i.e., when the transmission of data does not use a physical connection (such as copper cable or fiber optics), electromagnetic radiation is useful to transmit information over long distances without damaging the information due to noise and interference. Various techniques for digital transmission of data are known in the art. Typically, the desired information is encoded into a digital signal and then may be modulated onto a carrier wave and made part of a larger signal. The signal is then sent into a multiple-access transmission channel, and electromagnetic radiation, e.g., radio, infrared, and visible light, is used to send the signal. After transmission, the above process is reversed at the receiving end, and the information is extracted. Wireless data transmission may be, for example, via radio waves or via visible, IR or NIR optical link. Examples of wireless data transmission via radio waves include cellular phones, wireless LAN and microwave transmission. Examples of wireless data transmission via visible or NIR optical link include remote controls for televison and wireless data ports of laptop computers and personal digital assistants (PDAs).

None of the prior art systems provide an apparatus for wirelessly determining the homogeneity and potency of the components of a pharmaceutical mixture immediately prior to preparation of the dosage form. Moreover, none of the prior art systems described above provide an apparatus for determining the potency of the components of a pharmaceutical mixture while the pharmaceutical mixture is in a hopper. Accordingly, it is desirable to provide an apparatus that can assess the homogeneity and potency of the components of a pharmaceutical mixture in a hopper, detect stratification or non-uniformity of the mixture of the components immediately prior to preparation of the dosage form from the pharmaceutical mixture, and transmit this information wirelessly to a computer for analysis.

In accordance with a preferred embodiment of the invention, an apparatus is provided for detecting the homogeneity of a pharmaceutical mixture. The apparatus has a hopper that is situated within a production line of preparation of a pharmaceutical dosage form. The hopper contains a mixture of two or more pharmaceutical components. The mixture may, for example, be a granulation or a dry blend. A spectroscopic device (e.g., a spectrometer) is mounted to the hopper for measuring spectroscopic characteristics of the contents of the hopper. A processing device can be situated remote from and not physically coupled to the spectroscopic device, the processing device being adapted to analyze information regarding said spectroscopic characteristics of the mixture and derive therefrom information regarding the homogeneity and/or stratification of the mixture. The spectroscopic device measures the spectroscopic characteristics of the mixture within the hopper and wirelessly sends this information to the remote processing device, which derives information regarding the homogeneity and/or stratification of the mixture of pharmaceutical components. The wireless transmission of the spectroscopic characteristics can be done through infrared radiation or near infrared radiation, and the spectroscopic characteristics can be converted to digital signals prior to being transmitted. The preferred embodiments of this invention contemplate various configurations of the source of light or radiation, the detectors and the filtering devices, as well as various different and specific types of sources of light or radiation, detectors and the filtering devices.

In accordance with certain embodiments of the present invention, the spectroscopic device (e.g., a spectrometer) comprises at least one linear variable filter moved by a piezoelectric bimorph relative to a light source, such that said mixture in the hopper is irradiated with radiation in at least one specified band of wavelengths corresponding to the position of said at least one linear variable filter relative to said light source. In accordance with other aspects of this embodiment, the at least one variable filter includes a plurality of variable filters, and the detector includes a plurality of detectors, each of the plurality of variable filters passes light in a different band of wavelengths, each of the plurality of variable filters being associated with a corresponding one of the plurality of detectors.

BRIEF DESCRIPTION OF THE DRAWINGS

FIGS. 14A–B show an illustrative remote spectrometer for performing spectral scans.

FIGS. 18A–F show a further preferred embodiment of a remote spectrometer.

DETAILED DESCRIPTION OF THE INVENTION

Figure 1A:
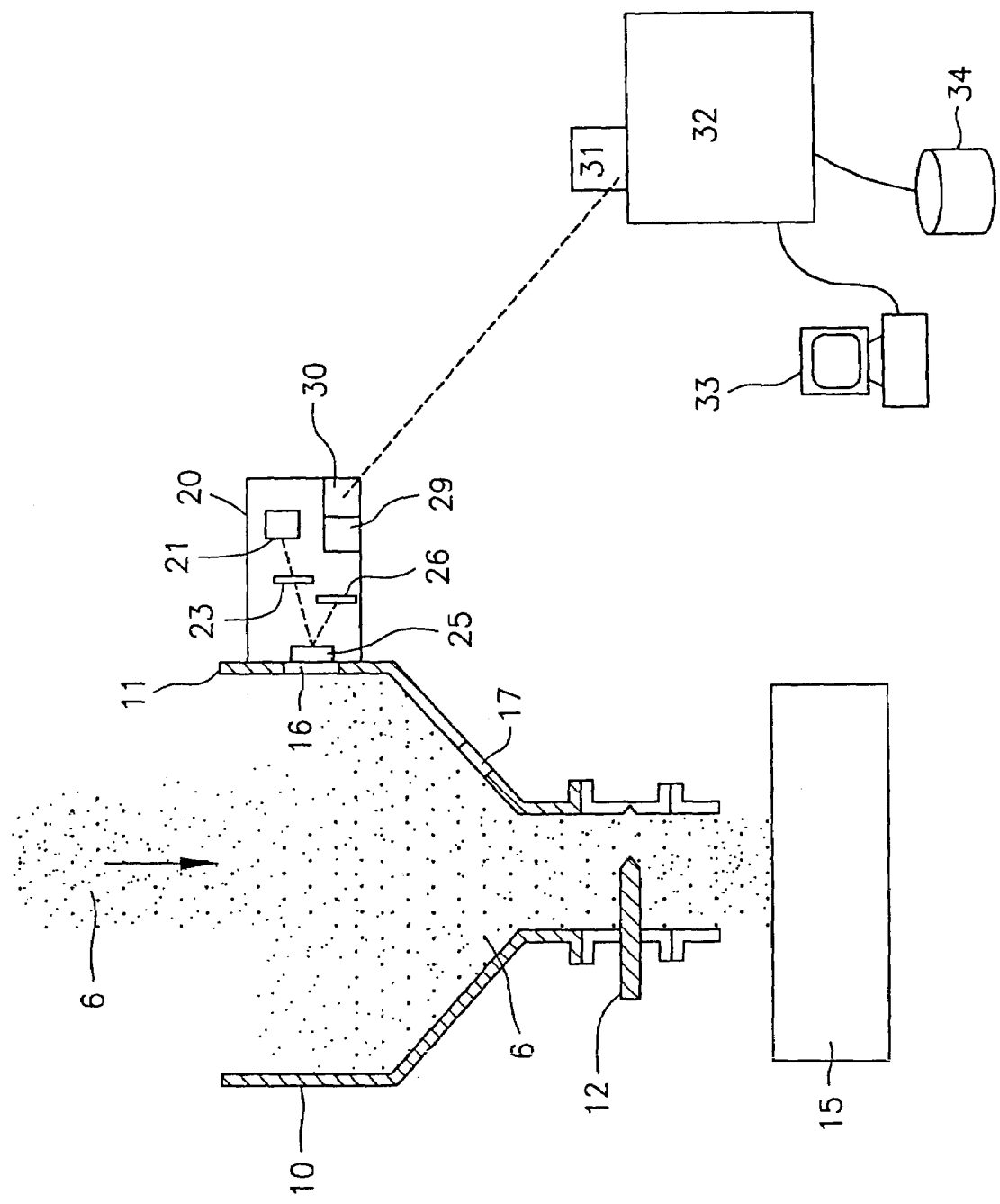
FIG. 1A shows a schematic representation of a first embodiment of the present invention in a pre-dispersive configuration.

FIG. 1A shows a schematic representation of a first embodiment of the present invention in a pre-dispersive configuration. One or more substances (which, may for example, be a granulation 6, a mixture or a pharmaceutical component) are fed into a hopper 10. Hopper 10 can be any one of the many different types of hoppers known to those skilled in the art, such as those manufactured by N.K. Engineering Co., or a hopper feeder, such as those manufactured by Garvey Corporation. The hopper 10 can be located in a production line comprising a mixer, a tableting press, and/or an encapsulating press. For example, the hopper can be located upstream of the mixer to feed a pharmaceutical mixer to the mixer, and/or upstream of a tableting (or an encapsulation press to feed a pharmaceutical mixer to the press. In certain embodiments, the hopper can be integrated into mixer, tableting press, and/or encapsulating.

In general, hopper 10 may have a valve 12 to accumulate a set amount of the granulation 6, or, if the substances fed into the hopper is a mixture of powders, a dry blend. It should be appreciated that although the end product discharged from the hopper 10 is referred to in the following discussion as granulation 6, it can be any conventional end product of a hopper, including, for example, a dry blend. Valve 12 can also be a knife valve or a butterfly valve, such as an ultra-sanitary butterfly valve made by Cobra International, to also prevent jamming and sticking of granulation 6 within hopper 10. In one embodiment, after granulation 6 has reached a pre determined volume, granulation 6 passes into a tableting/encapsulating machine 15. Tableting/encapsulating machine 15 can be any of the known machines in the art, such as a single rotary tableting machine, a double rotary tableting machine, a GMP rotary tableting machine (for example, manufactured by Gaylord), a Slugging/Bolus press, a high speed tablet press, an oscillating granulator (for example, manufactured by Victory Enterprises), etc. In certain embodiments, the present invention may use tablet presses, such as those manufactured by Niro Inc., Se Jong Machinery Co. or Cadmach. In certain other embodiments, hopper 10 forms a part of tableting/encapsulating machine 15.

A spectrometer (which is shown schematically at 20) is mounted to hopper 10. A variety of different types of spectrometers are known in the art, such as grating spectrometers, FT (Fourier transformation) spectrometers, Hadamard transformation spectrometers, AOTF (Acousto Optic Tunable Filter) spectrometers, diode source spectrometers, filter-type spectrometers, scanning dispersive spectrometers, nondispersive spectrometers, and others as discussed below, and any of these may be used with the present invention.

In certain embodiments, a plurality of spectrometers 20 may be mounted to the hopper 10. Referring to FIG. 1(g), granulation 6 follows a path 1000 (preferably a vertical path as shown) from the input 1010 of the hopper 10 to the output 1020 of the hopper. The plurality of spectrometers 10 can be mounted to the hopper in various configurations. For example, the spectrometers can be mounted along a plane 1001 perpendicular to the path 1000 as described below with regard to FIG. 3 to determine whether the homogeneity and/or moisture content of the granulation varies at a particular level of the hopper 10. Alternatively, the spectrometers can be spaced apart along the path 1000 (e.g., vertically spaced apart) to determine whether the homogeneity and/or moisture content of the granulation varies at different points along the path 1000.

Filter-type spectrometers, for example, utilize a light source (e.g., tungsten filament lamp) to illuminate a rotating opaque disk, wherein the disk includes a number of bandpass optical filters or beam splitters. The disk is then rotated so that each of the bandpass filters passes between the light source and the sample, and an encoder indicates which optical filter is presently under the light source. The filters interact with the light from the light source so that only a selected wavelength range passes through the filter to the sample. Optical detectors are positioned to detect light which either is reflected by the sample (to obtain a reflectance spectra) or is transmitted through the sample (to generate a transmittance spectra). The amount of detected light is then measured, thereby providing an indication of the amount of absorbance of the light by the sample.

Diode Source spectrometers use infrared emitting diodes (IREDs) as sources of near infrared radiation. A plurality (for example, eight) of IREDs are arranged over a sample work surface to be illuminated for quantitative analysis. Near-infrared radiation having a narrow bandwidth (e.g. 30–50 nm) emitted from each IRED impinges upon an accompanying optical filter. Each optical filter is a narrow bandpass filter which passes NIR radiation at a different wavelength. NMR radiation passing through the sample is detected by a detector (such as a silicon photodetector). The amount of detected light is then measured, thereby providing an indication of the amount of absorbance of the light by the substance under analysis.

Acousto Optical Tunable Filter spectrometers utilize a radio frequency (RF) signal to generate acoustic waves in a $TeO_2$ crystal. A light source transmits a beam of light through the crystal, and the interaction between the crystal and the RF signal splits the beam of light into three beams: a center beam of unaltered white light and two beams of monochromatic and orthogonally polarized light. A sample is placed in the path of one of the monochromatic beam detectors, which are positioned to detect light that either is reflected by or transmitted through the sample, and the amount of detected light is then measured, thereby providing an indication of the amount of absorbance of the light by the sample. The wavelength of the light source can be incremented across a wavelength band of interest by varying the RF frequency.

In grating monochromator spectrometers, a light source transmits a beam of light through an entrance slit and onto a diffraction grating (the dispersive element) to disperse the light beam into a plurality of beams of different wavelengths (i.e., a dispersed spectrum). The dispersed light is then reflected back through an exit slit onto a detector. By selectively altering the path of the dispersed spectrum relative to the exit slit, the wavelength of the light directed to the detector can be varied. The amount of detected light is then measured, thereby providing an indication of the amount of absorbance of the light by the sample. The width of the entrance and exit slits can be varied to compensate for any variation of the source energy with wave number.

In an ATR (attenuated total reflectance) spectrometer, radiant energy incident on an internal surface of a high refractive index transparent material is totally reflected. When an infrared absorbing material is in optical contact with the totally internally reflecting surface, the intensity of the internally reflected radiation is diminished for those wavelengths or energies where the material absorbs energy. Since an internal reflecting surface is essentially a perfect mirror, the attenuation of this reflected intensity by a material on its surface provides a means of producing an absorption spectrum of the material. Such spectra are called internal reflection spectra or attenuated total reflection (ATR) spectra.

The material with the high index of refraction that is used to create internal reflection is called an internal reflection element (IRE) or an ATR crystal. The attenuation of the internally reflected radiation results from the penetration of the electro-magnetic radiation field into the matter in contact with the reflection surface. This field was described by N. J. Harrick (1965) as an evanescent wave. It is the interaction of this field with the matter in contact with the IRE interface that results in attenuation of the internal reflection. Though not absolutely necessary, pressure on an ATR crystal may improve performance by increasing the amount of the substance (e.g. granulation 6) that is in contact with the IRE. Pressure may be generated by placing the crystal in neck region 98 of hopper 10, where higher pressure exists due to the weight of granulation 6 above. Alternatively, the ATR crystal may be mounted on a piston device that presses into granulation 6 when in a forward position so that the crystal only scans when in this forward position.

Any such spectrometer may be suitably used with the present invention. In one embodiment, as shown in FIGS. 1A–E, an aperture or window 16 is formed through a wall 11 of hopper 10, and spectrometer. 20 is mounted to hopper 10 about aperture or window 16. In certain embodiments, a transparent element 25 such as a lens, can be located outside hopper 10 as part of spectrometer 20 and can serve to focus and/or direct light onto granulation 6 within hopper 10. In other embodiments, transparent element 25 is fit into a slit or indentation in wall 11 of hopper 10 adjacent to window 16 or, alternatively, can be used instead of window 16. In an ATR embodiment of the present invention, the window 16 can function as the internal reflection element.

Figure 1B:
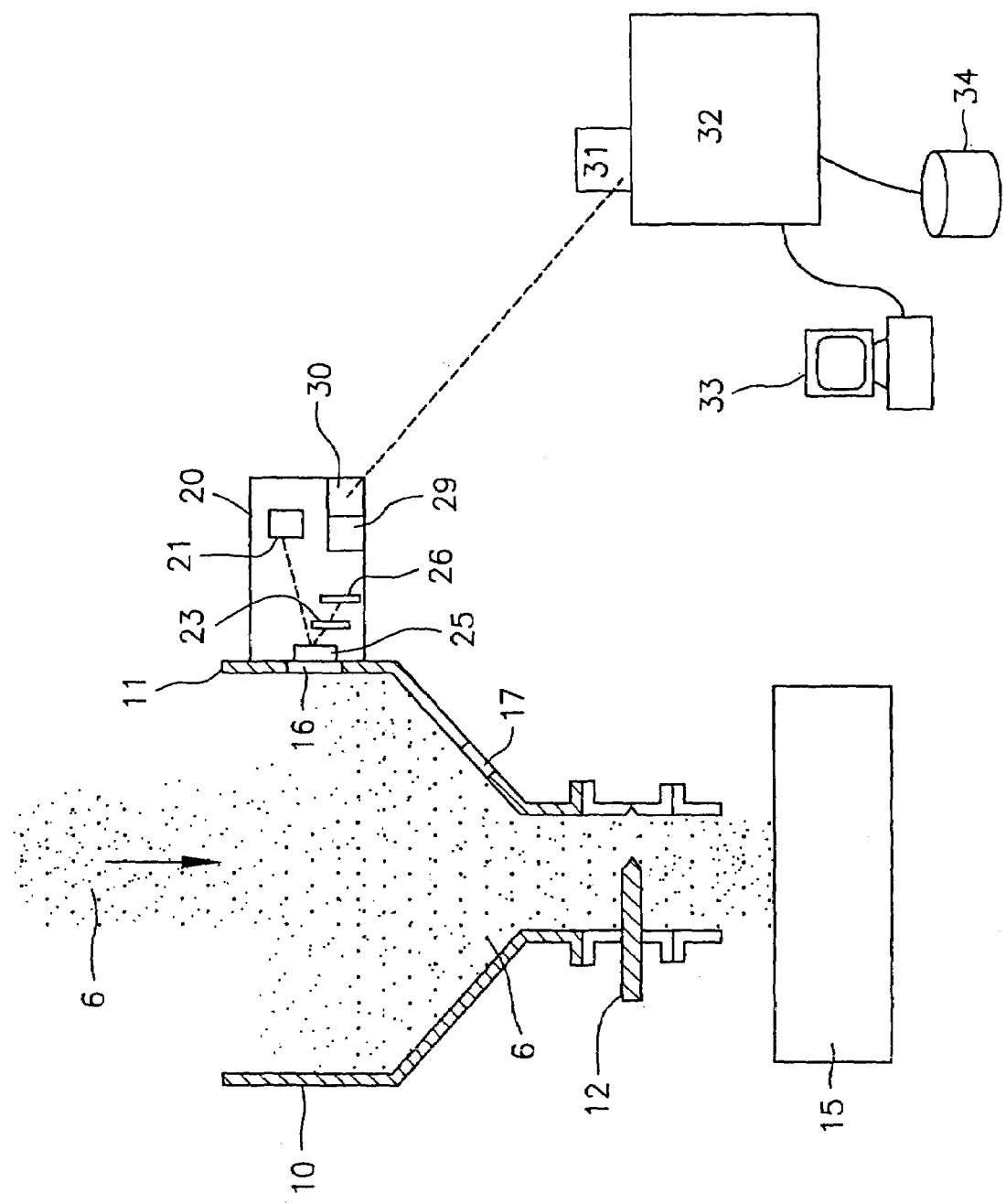
FIG. 1B illustrates a schematic representation of a first embodiment of the invention in a post-dispersive configuration.
Figure 1C:
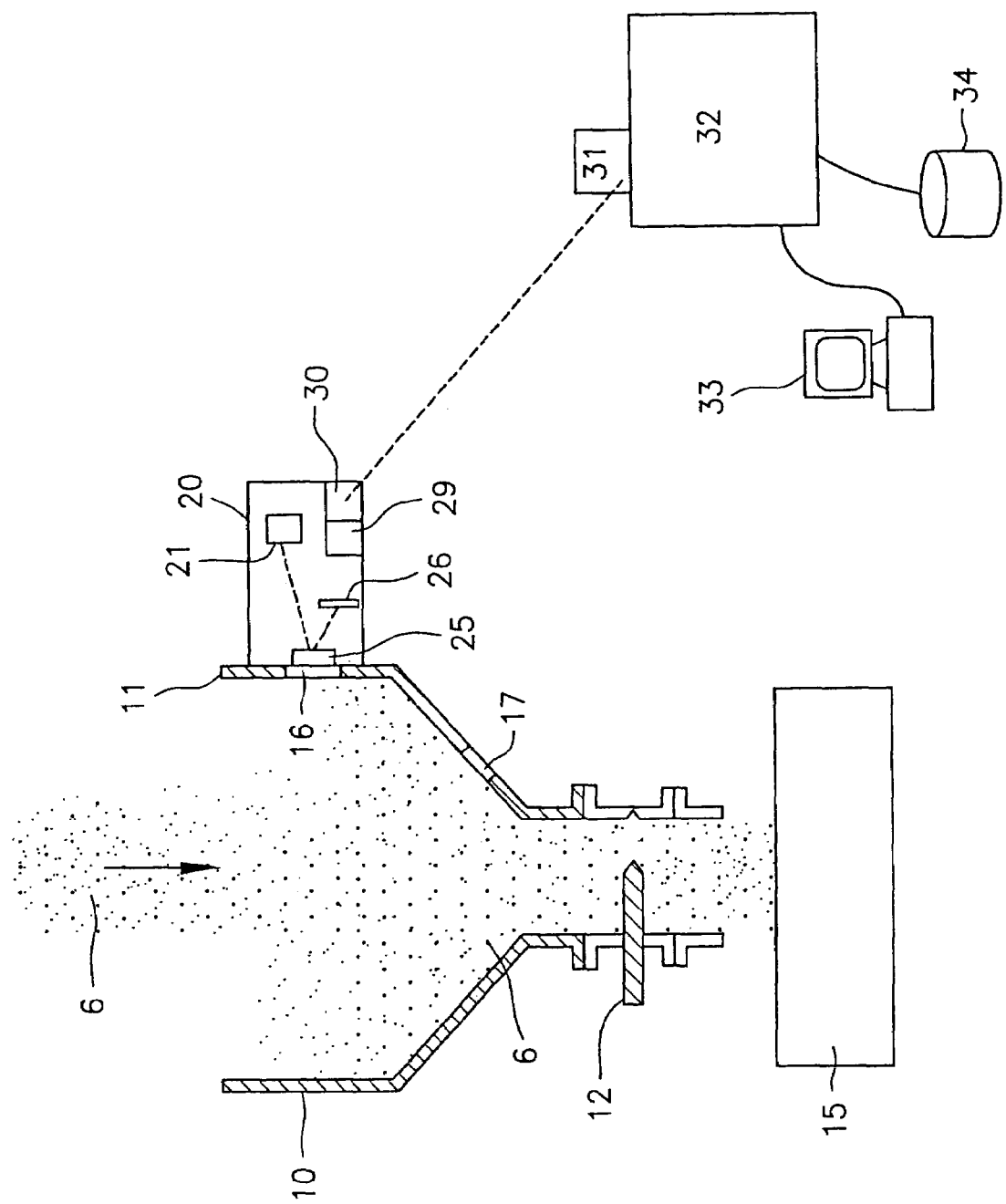
FIG. 1C illustrates a schematic representation of a first embodiment of the invention in a configuration that uses a monochromatic source of light and no filter.
Figure 1D:
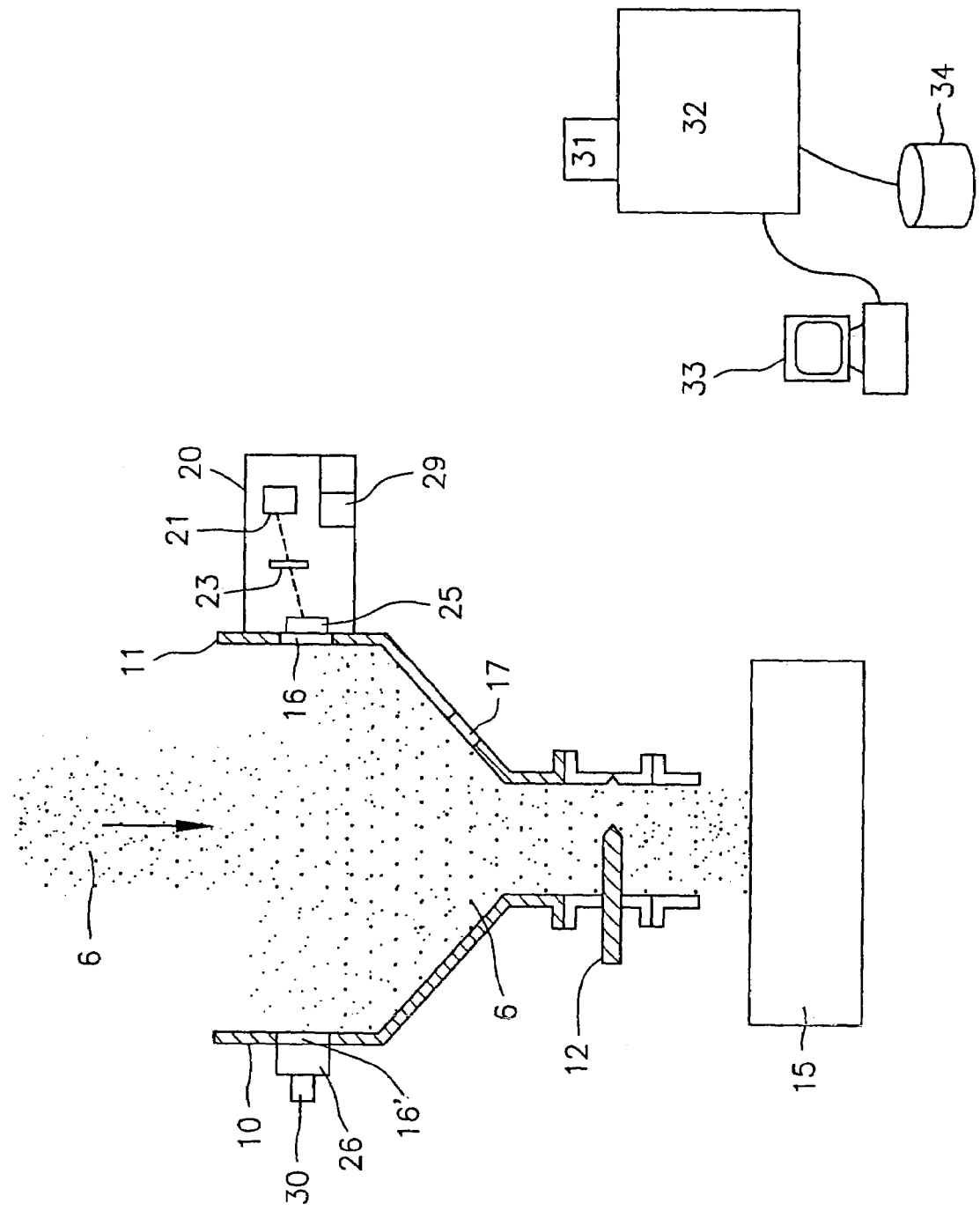
FIG. 1D illustrates a schematic representation of a first embodiment of the invention wherein the light source and detector are configured for a transmittance measurement.
Figure 1E:
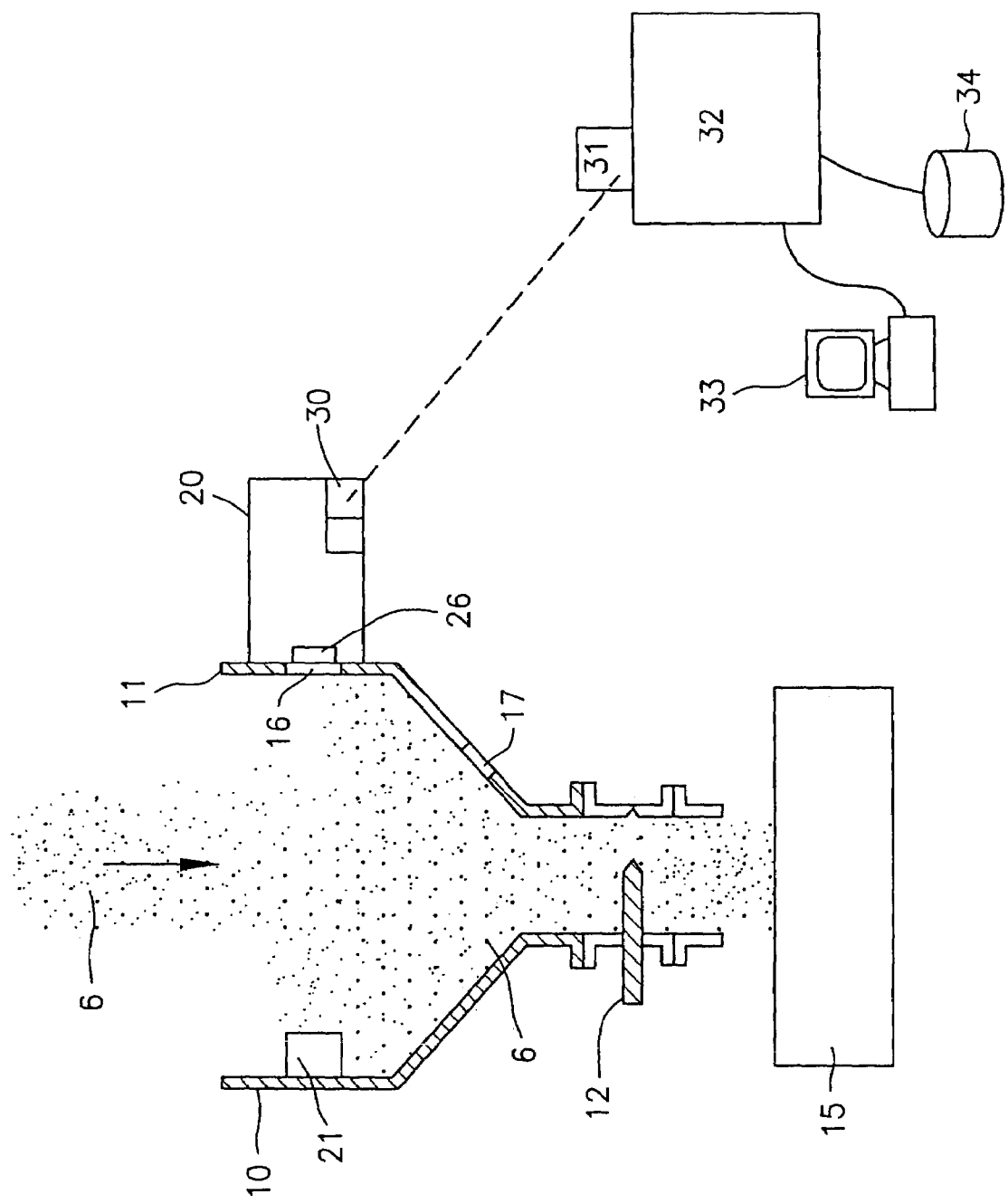
FIG. 1E shows a schematic representation of a first embodiment of the invention wherein the light source and detector are mounted inside the hopper.
Figure 1F:
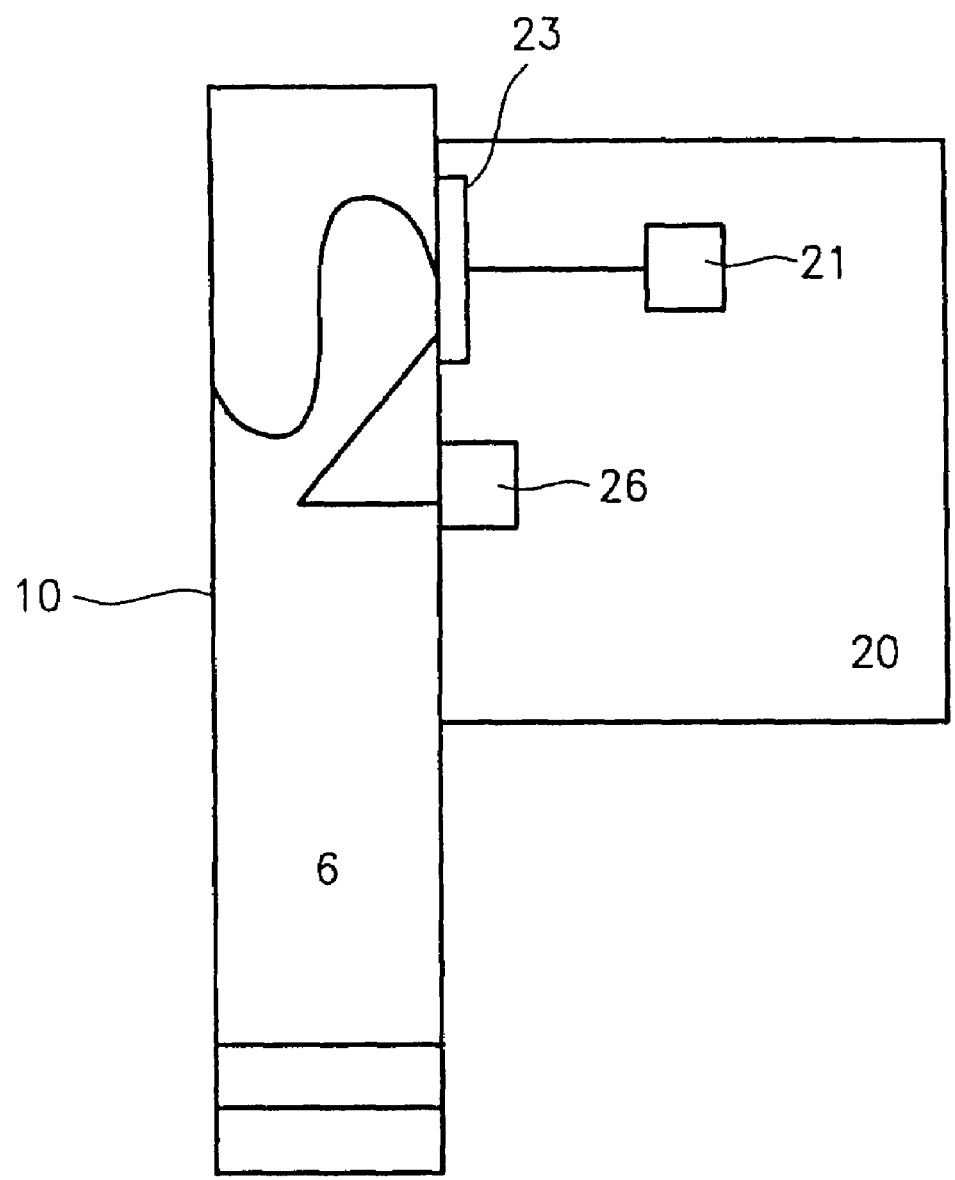
FIG. 1F shows a schematic representation of a first embodiment of the invention wherein the light source and detector are configured for a reflectance measurement.
Figure 1G:
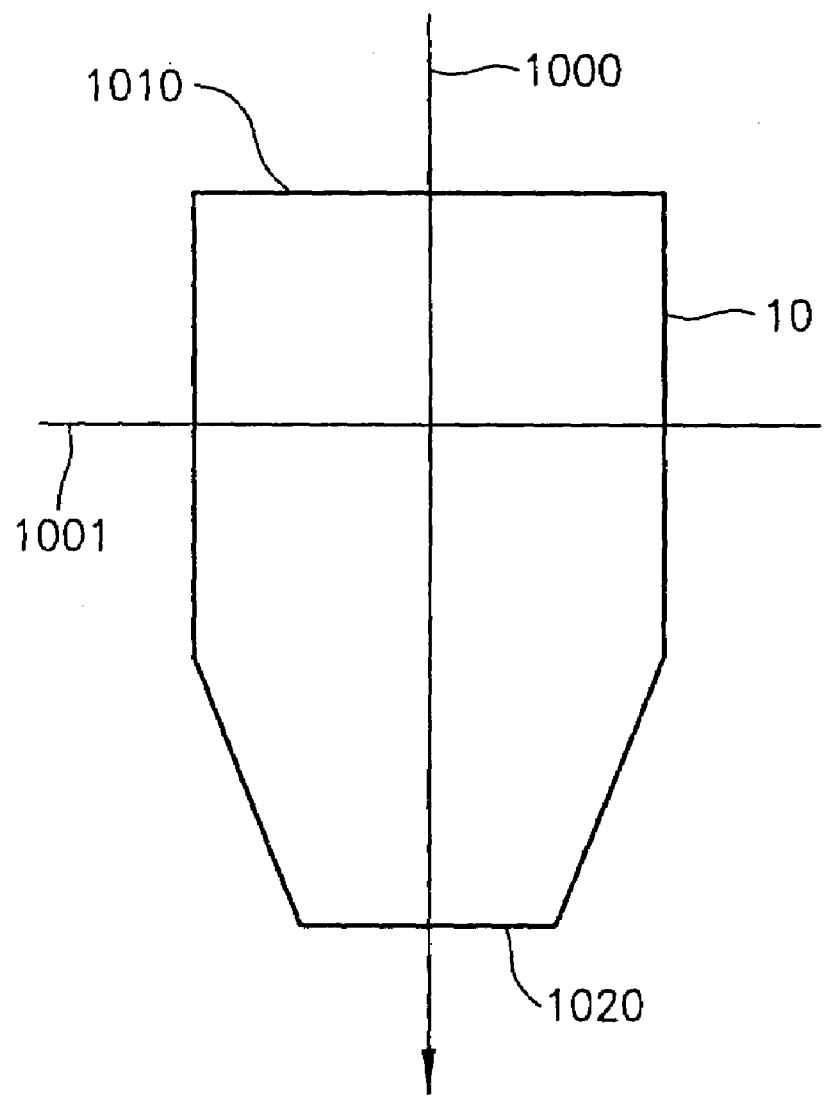
FIG. 1G shows a schematic representation of an embodiment of the present invention wherein the granulation follows a path from the input of the hopper to the output of the hopper.
Figure 1H:
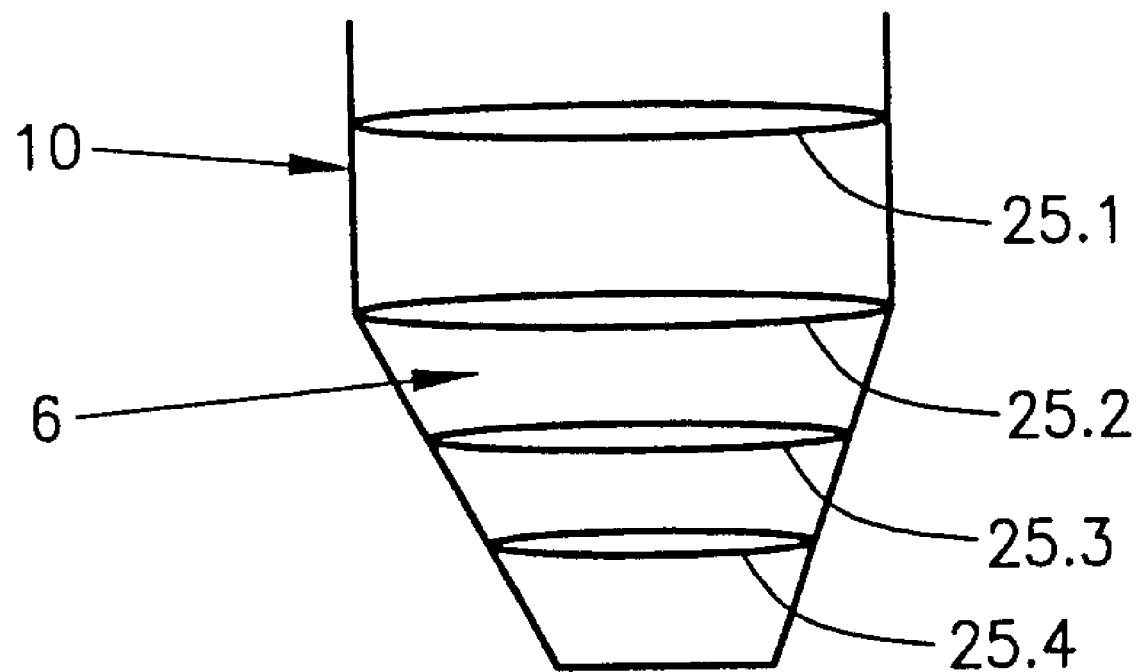
FIG. 1H shows a schematic representation of another embodiment of the present invention.

Referring to FIG. 1H, in a further embodiment of the present invention, a plurality of IREs 25.1–25.4 are secured to the interior surface of the hopper. In this embodiment, each IRE extends laterally across the interior surface of the hopper 10. Preferably, each IRE extends substantially across the entire circumference (in the case of a circular or elliptically shaped interior surface), or substantially across each interior wall (in the case of an interior surface shaped as a polygon) of the hopper 10, and the IRE's 25.1–25.4 are vertically spaced apart. In this manner, each IRE will detect the average spectroscopic characteristics of the substance at its corresponding vertical level. By comparing the detected spectroscopic characteristics of IRE's 25.1 through 25.4, differences in homogeniety and/or moisture in different portions of the hopper can be determined. Examples of suitable IRE's include various fused silica know to be effective in the infrared region.

In one preferred embodiment, spectrometer 20 has a light source 21, a light filtering device 23, a transparent element 25 and a detector 26. Light source 21 generates a beam of light or radiation that passes through light filtering device 23. Light filtering device 23 separates the beam of polychromatic light into a monochromatic beam (or a beam having a narrower band of wavelengths than the polychromatic beam that is generated by light source 21 has), which then passes through a transparent element 25, such as a lens, that is set within or adjacent to window 16 in wall 11 of hopper 10, as illustrated in FIG. 1A. After passing through transparent element 25, the beam of light or radiation impinges on granulation 6. The reflected light is then absorbed by detector 26, which converts the detected beam of radiation (which now comprises the spectroscopic characteristics of the material in the hopper 10) into a digital signal. In an embodiment of the present invention utilizing an ATR spectrometer, the transparent element 25 can be the IRE and the beam could reflect off the interface between granulation 6 and spectrometer transparent element 25 (e.g., where the granulation 6 and transparent element 25 contact one another). This configuration of the embodiment of FIG. 1A is "pre-dispersive" because the light generated by light source 21 passes through light filtering device 23 and is filtered to a monochromatic beam prior to it being dispersed by or reflected off the substance being analyzed, i.e., granulation 6.

In certain embodiments, detector 26 can be a photographic plate, a photoemissive detector, an imaging tube, a solid-state detector or any other suitable detector. Light filtering device 23 can be a prism, a grating filter (which is an optical device with a surface ruled with equidistant and parallel lines for the purpose of filtering light), an interferometer, or any other suitable filter. In an FTIR embodiment, a beam splitter and a movable mirror can be incorporated into spectrometer 20.

Preferably, spectrometer 20 and transparent element 25 are located above valve 12, either at a position adjacent to window 16 or at a position adjacent to window 17, as shown in FIG. 1A, or elsewhere suitable. However, in certain embodiments, spectrometer 20 can be located below valve 12. Wherever spectrometer 20 is located, embodiments utilizing a single spectrometer can be useful for collecting spectra from a "sample stream" of granulation 6 as it passes by transparent element 25. In addition, in a multiple reading embodiment of the invention, wherein multiple spectroscopic scans of the composition are taken, some of a plurality of spectrometers 20 or transparent elements 25 can be placed above valve 12, while others can be placed below valve 12. In the multiple reading embodiment, the different readings taken at different steps in the process can be compared with each other in order to locate a problem within the manufacturing process. The material for the transparent element can be selected as a function of the desired wavelength to be used. For example, glass is transparent up to 2200 nm, sapphire is transparent up to 5 microns, and barium fluoride is transparent up to 20 microns.

In this embodiment, as illustrated in FIG. 1A, spectrometer 20 is in wireless communication with a processing device 32 (which, in this example, is a remote processing device) such that spectrometer 20 is capable of wirelessly transmitting spectral data to processing device 32 at a remote location. In one embodiment, detector 26 converts the reflected beam into a digital signal that is then wirelessly transmitted to remote processor 32, where the reflected beam is analyzed. The digital signal generated by detector 26 of spectrometer 20 is first fed into a transmitter 30 located in or attached to spectrometer 20 and coupled to detector 26. Transmitter 30 then transmits the digital signal wirelessly to a receiver 31, which receives the digital signals on behalf of processing device 32. The digital signal can be transmitted from transmitter 30 to receiver 31 by any known technique in the wireless transmission art, as will be discussed in greater detail below.

FIG. 1B illustrates a schematic representation of the first embodiment of the invention in a post-dispersive configuration. In this embodiment, the beam of light generated by light source 21 first impinges upon granulation 6 and only then passes through light filtering device 23. After passing through light filtering device 23, the reflected light is absorbed by detector 26. This configuration is "post-dispersive" because the light generated by light source 21 passes through light filtering device 23 and is filtered to a monochromatic beam (or a beam having a narrower band of wavelengths than the polychromatic beam that is generated by light source 21 has) after is has been dispersed by or reflected off the substance being analyzed, i.e., granulation 6.

FIG. 1C illustrates a schematic representation of the first embodiment of the invention in a configuration wherein spectrometer 20 does not comprise a light filtering device 23 at all. In this embodiment, because light filtering device 23 is not present, light generated by light source 21 is not passed through a filtering device either prior to being reflected off granulation 6 or after being reflected off granulation 6. Instead, light source 21 itself generates a beam of monochromatic light. Light source 21 can thus be, for example, a monochromatic laser.

FIG. 1D illustrates a schematic representation of a first embodiment of the invention wherein light source 21 and detector 26 of spectrometer 20 are configured for a transmittance measurement. Light source 21 generates a beam of light, which passes through light filtering device 23 and onto granulation 6. Transparent element 25 can also be included within this configuration, in order to focus or direct light onto granulation 6. The beam of light then impinges detector 26, where the spectral data is measured. Alternatively, filtering device 23 could be situated adjacent to detector 26 (not shown), rather than adjacent light source 21, so that filtering of the light beam is performed post-dispersively, rather than pre-dispersively, as shown in FIG. 1D. Detector 26 can be situated inside wall 11 of hopper 10 (not shown) or outside wall 1, in which case light would exit hopper 10 through window 16'. Whether light filtering device 23 is located adjacent to light source 21 or to detector 26, filtering device 23 and/or transparent element 25 could alternatively form a portion of wall 11 of hopper 10. In this embodiment, detector 26 may communicate with transmitter 30 or processing device 32 by a physical connection (e.g., a copper wire) or wirelessly, as discussed below.

FIG. 1E shows an embodiment of the invention in a variation of FIG. 1D wherein the positions of light source 21 and detector 26 are effectively reversed. In this embodiment, light source 21 is still situated on the opposite side of hopper 10 from detector 26 in order to facilitate transmittance spectrometry. As shown in FIG. 1E, however, detector 26 is located adjacent to spectrometer 20. In one version of this embodiment, both light source 21 and detector 26 can be mounted inside hopper 10, most preferably on opposite sides of hopper 10. Window 16 need not be present in this version of the embodiment, since light source 21 is inside hopper 10, and light generated by light source 21 passes through granulation 6 prior to being detected by detector 26. As shown in FIG. 1E, detector 26 maybe mounted outside wall 11 of hopper 10, within spectrometer 20, or behind window 16 in wall 11.

FIG. 1F shows a schematic representation of a first embodiment of the invention, in a side view of hopper 10, wherein light source 21 and detector 26 are configured for a reflectance measurement. Light source 21 generates a beam of light, which passes through light filtering device 23 and onto granulation 6. No transparent element 25 is used. A portion of the beam of light reflected off the granulation 6 continues onto detector 26, where the spectral data is measured.

Figure 2:
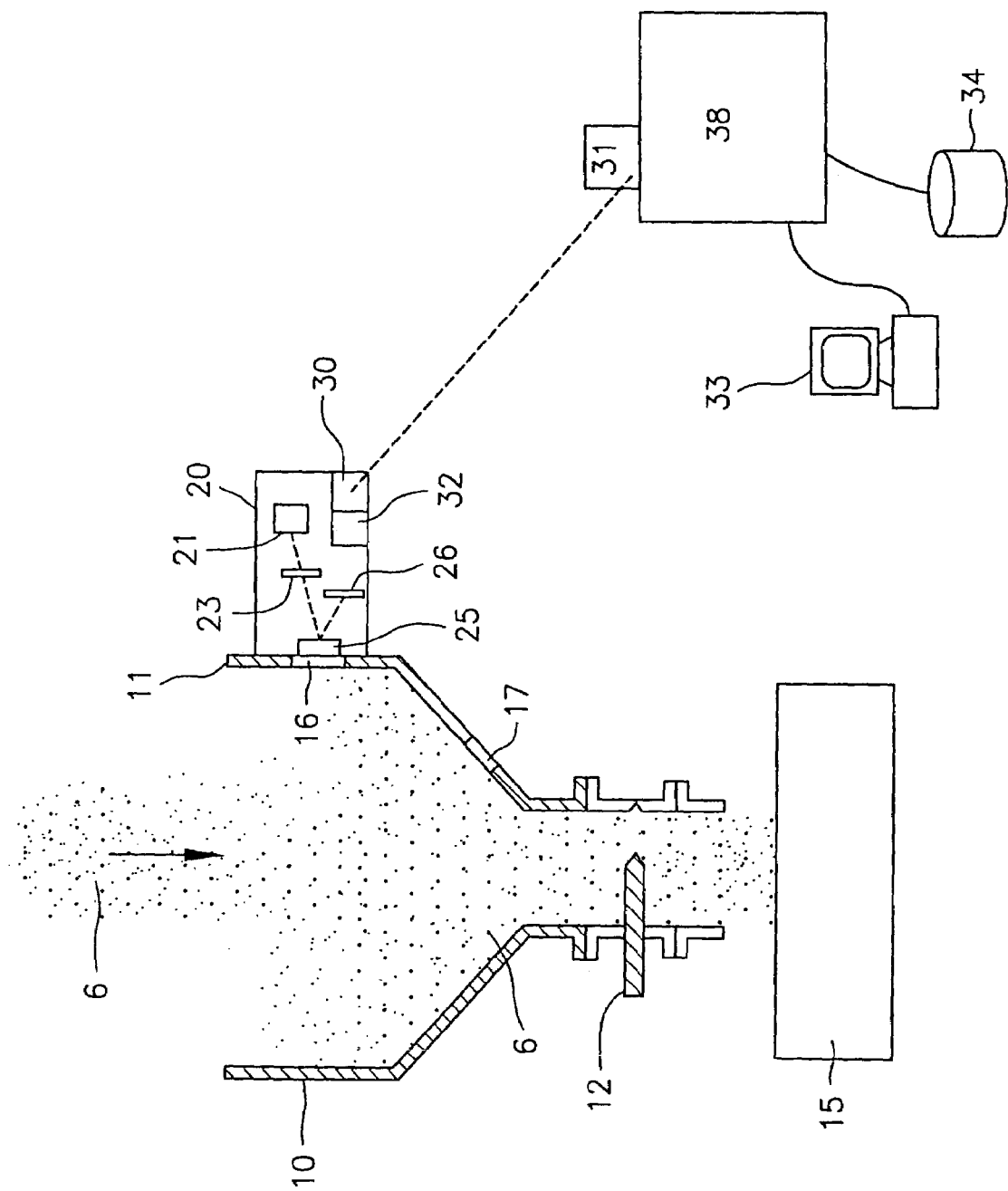
FIG. 2 shows a schematic representation of a second embodiment of the invention in a mode wherein the processing device is physically connected to spectrometer.

FIG. 2 illustrates a second embodiment of the invention in a mode wherein processing device 32 is physically connected to spectrometer 20, rather than being remotely separated therefrom, as shown in FIGS. 1A–1F. In this embodiment, detector 26 converts the reflected beam into a digital signal that is then transmitted to processor 32 that is physically within, attached to or adjacent to spectrometer 20, where the reflected beam is analyzed. The connection between processing device 32 and detector 26 can be by conventional cables, wires or data buses, in which case transmission takes place through such physical connections. In this embodiment, there is no need for the digital signal generated by detector 26 to be fed into a transmitter located in or attached to spectrometer 20 and then transmitted wirelessly to a receiver on behalf of processing device 32.

However, a transmitter 30 may still be present and located in or attached to spectrometer 20 and coupled to processor 32. The digital signal that is analyzed and/or transformed by processing device 32 can be then fed to transmitter 30 for transmission to receiver 31 via a wireless connection. Transmitter 30 transmits the digital signal of data processed by processing device 32 wirelessly to receiver 31, which receives the digital signals on behalf of a remote processing device 38 for further processing. As before, the digital signal can be transmitted from transmitter 30 to receiver 31 by any known technique in the wireless transmission art, as will be discussed in greater detail below. Processing device 32 may compress the digital signal so that it can be transmitted more efficiently or may modify the digital signal to facilitate error correction/detection, such as by inserting hamming code bits or error checking bits into the digital signal. The receiver can be physical connected to other devices (e.g., another processing device or display device).

Figure 3:
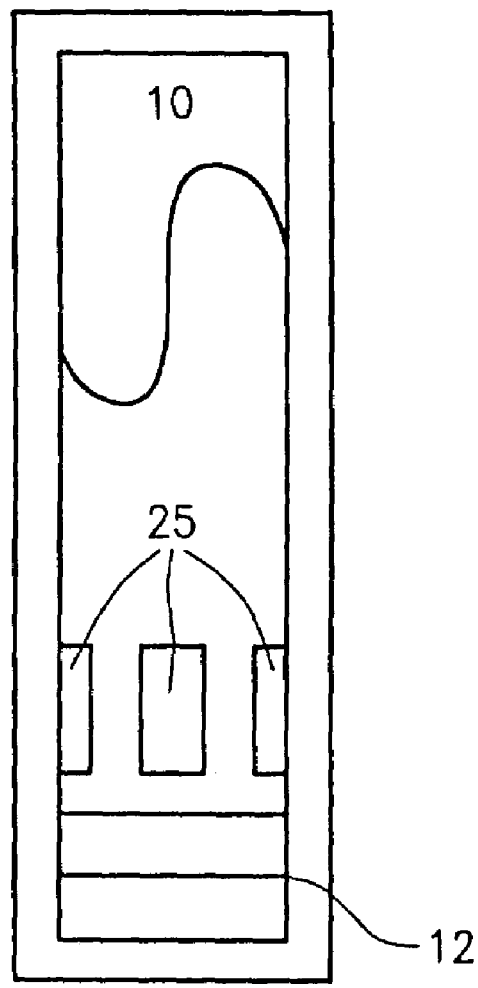
FIG. 3 shows a schematic representation of a third embodiment of the present invention wherein a plurality of spectrometers or transparent elements are used.

FIG. 3 shows a third embodiment of the invention wherein a plurality of spectrometers 20 or transparent elements 25 are disposed about the circumference of hopper 10 (e.g., along the plane 1001 of FIG. 1G). In this embodiment, each transparent element 25 can be optically connected to a separate spectrometer 20. Thus, spectroscopic scans of the composition at different positions or angles in hopper 10 can be taken. In this embodiment, each of the plurality of spectrometers 20 situated about the circumference of hopper 10 can be any of the embodiments discussed above, and as shown in FIGS. 1A–1F and 2, or as discussed below. Thus, the various spectrometers can derive data regarding granulation 6 through may variations and embodiments, so as to obtain readings that are verifiably accurate though various different techniques.

With further reference to FIG. 3 and FIGS. 1A and 1B, in an embodiment of the present invention, plurality of spectrometers 20 may be located in neck region 98 of hopper 10, so that light sources 21 flood the neck region with large amounts of light. A "ring light" may thus be provided. Large amounts of light provide a relatively large signal-to-noise ratio for spectral analysis purposes. Such an embodiment would be especially useful for analyzing the homogeneity of granulation 6. Light sources 21 could be NIR light emitting diodes (LEDs), for example, since such devices generate relatively little heat. Detectors 26 for each spectrometer 20 may be diode arrays or linear variable filter detectors (such as the MicroPac family of products available from OCLI), for example. Alternatively, detectors 26 could each include a number of individual diodes having a respective filter 23 for excluding all but a desired wavelength of light, as in the embodiment shown in FIG. 1B. In this way, intensity values at different wavelengths may be measured for each position on hopper 10. In other embodiments of the present invention, a fiber optic bundle split into individual optical fibers, as shown in FIG. 4 below, could be used as the light source for flooding neck region 98 with light.

Figure 4:
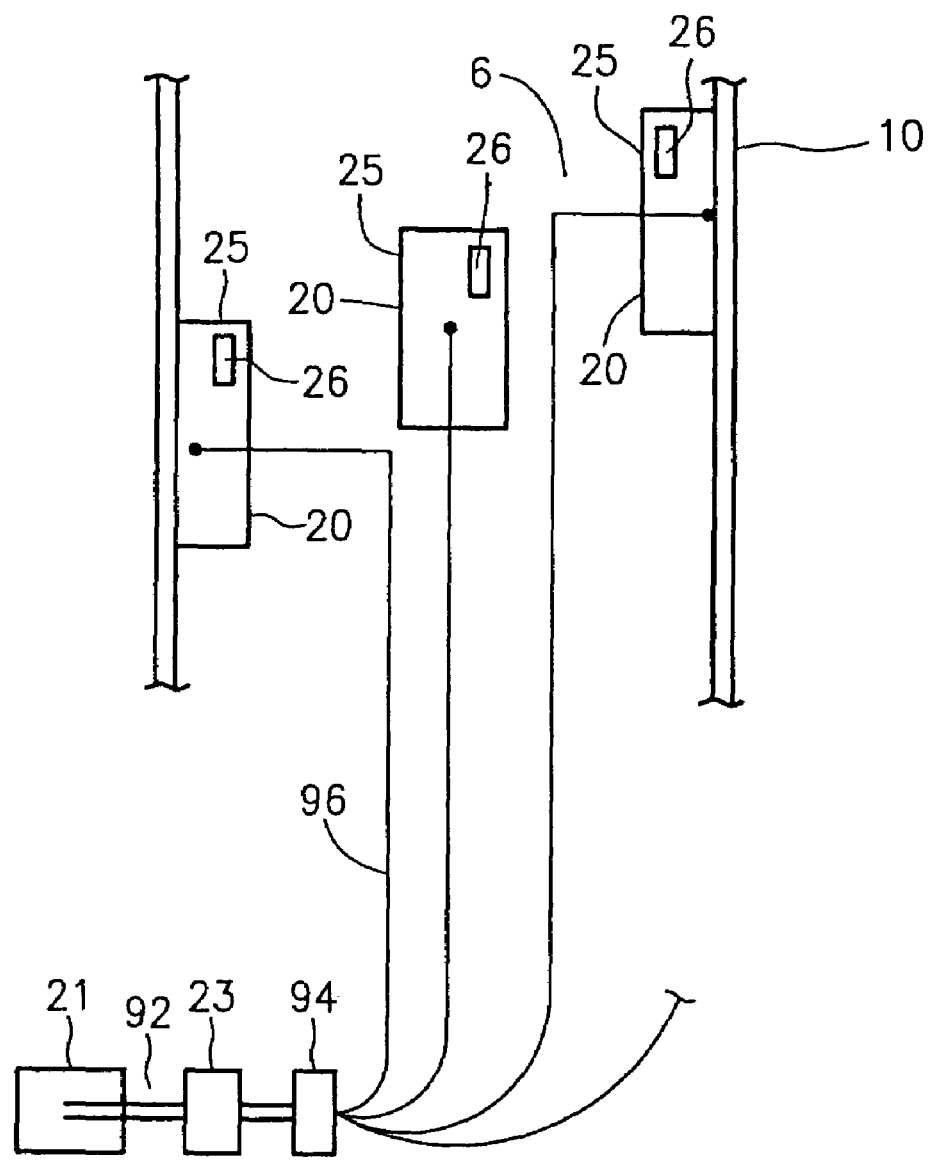
FIG. 4 shows a schematic representation of an embodiment of the present invention wherein a fiber optic bundle is used as a light source for illuminating multiple positions.

FIG. 4 shows another embodiment of the invention wherein a plurality of spectrometers 20 or transparent elements 25 are disposed about the circumference of hopper 10. This embodiment may be especially useful for analyzing for stratification in granulation 6. In this embodiment, light source 21 includes fiber optic bundle 92 optically connected to filtering, or monochromator, device 23. Filtering device 23 may be a grating, interferometer, filter wheel, or other suitable device for producing a monochromatic beam of light in each fiber of fiber optic bundle 92. Splitter device 94 is provided for splitting fiber optic bundle 92 into a plurality of individual fibers 96, which illuminate respective multiple positions, or angles, in hopper 10 via respective transparent elements 25. Respective detectors 26 are provided at each position or angle in hopper 10 for detecting light diffusively reflected, transmitted, etc., from granulation 6. Any desired number of spectrometers 20, and hence, of illumination and detection (sampling) positions on hopper 10, may be provided situated in a desired configuration about the circumference of the hopper. Moreover, the spectrometers may be positioned at different longitudinal levels on hopper 10, as shown in FIG. 4.

Figure 5:
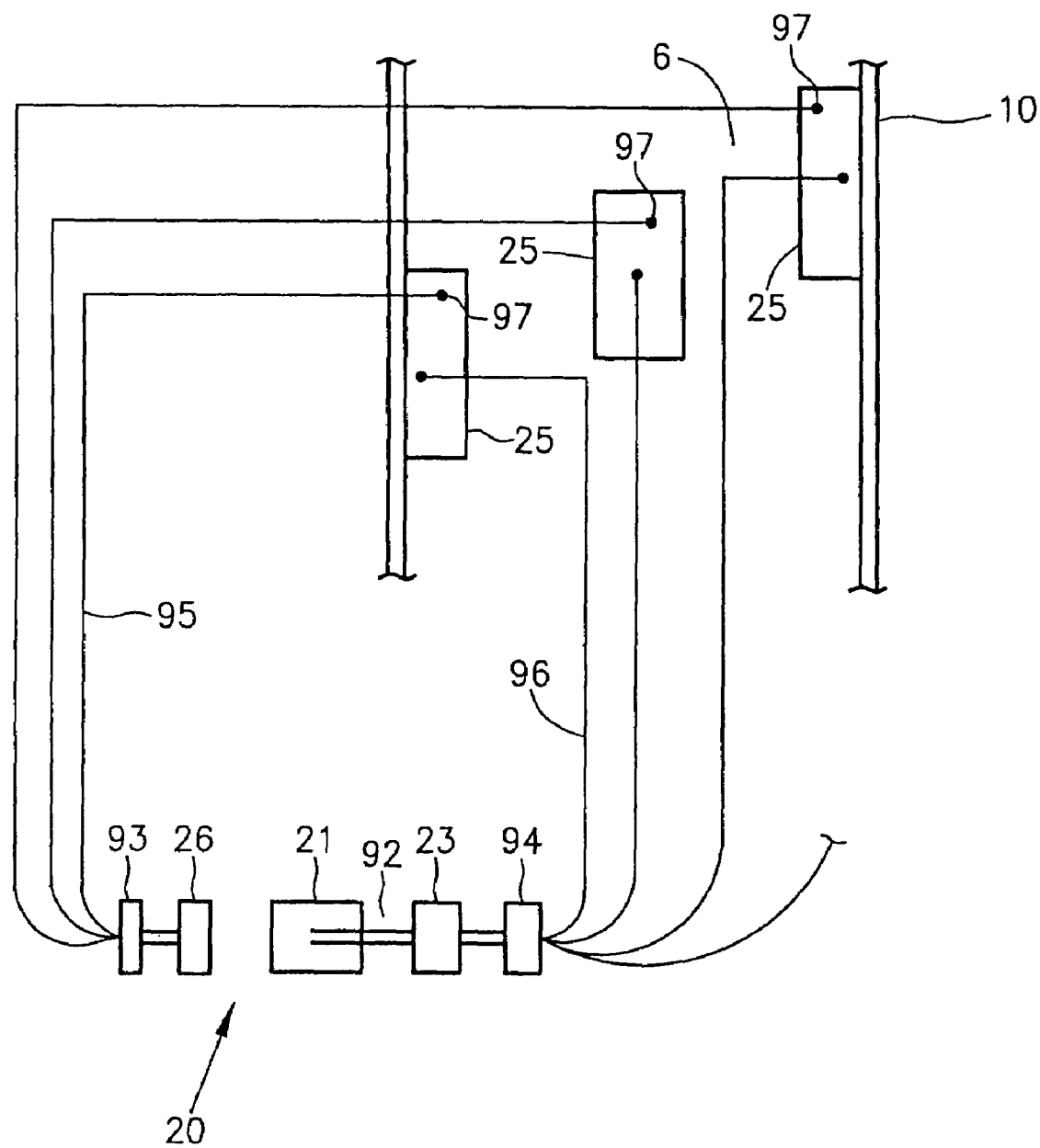
FIG. 5 shows a schematic representation of an embodiment of the present invention wherein in a single detector is interfaced to multiple fiber optic light guides.

FIG. 5 shows an embodiment of the invention having a single spectrometer 20 with a plurality of transparent elements 25 disposed as different longitudinal levels about the circumference of hopper 10. This embodiment, like the embodiment shown in FIG. 4, may be especially useful for analyzing for stratification in granulation 6. In this embodiment, like that shown in FIG. 4 and discussed above, light source 21 including fiber optic bundle 92 is provided. Fiber optic bundle 92 is optically connected to filtering, or monochromator, device 23. Filtering device 23 may be a grating, interferometer, filter wheel, or other suitable device for producing a monochromatic beam of light in each fiber of fiber optic bundle 92. Splitter device 94 is provided for splitting fiber optic bundle 92 into plurality of individual fibers 96, which illuminate respective multiple positions, or angles, in hopper 10 via respective transparent elements 25.

In the embodiment shown in FIG. 5, single detector 26 is provided. Detector 26 maybe a photo diode array or a single element detector combined with a monochromator interferometer, for example. Switching device 93 interfaces detector 26 with fiber optic light guides 95, each connected to a respective sampling position 97 at a respective transparent element 25. Each fiber optic light guide 95 receives diffusively reflected or transmitted, etc., light from granulation 6. Switching device 93 selects one sampling position 97 at a time and presents the received light to detector 26. This embodiment may be used to read out each sampling position 97 in a desired sequence in a relatively short period of time. Any desired number of sampling positions 97 may be provided situated in any desired configuration about hopper 10. In other embodiments of the present invention (not shown) respective individual light sources 21 may be provided for each transparent element 25, instead of using splitter device 94 plurality of individual fibers 96.

Figure 6:
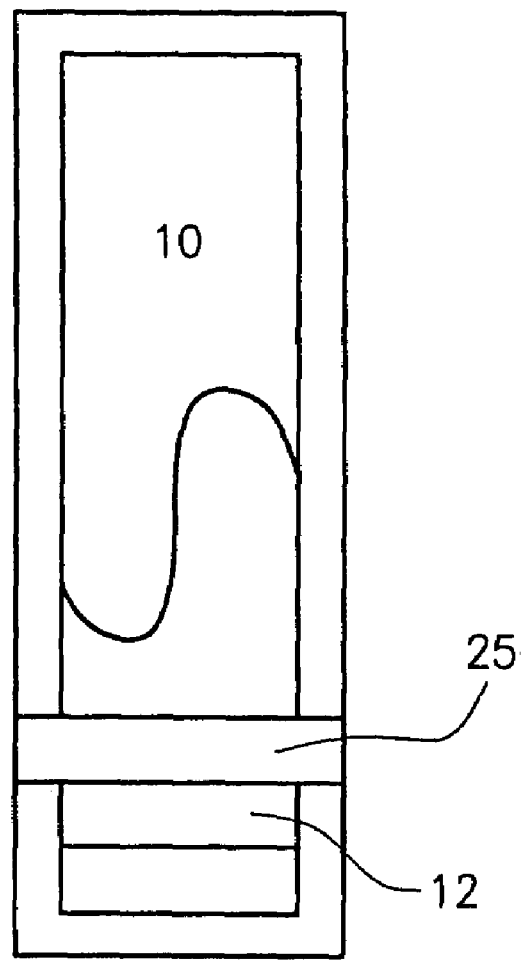
FIG. 6 shows a schematic representation of an embodiment of the present invention wherein the spectrometer transparent element is disposed on a top surface of a hopper valve.

FIG. 6 shows a fourth embodiment of the invention wherein spectrometer transparent element 25 is embedded in the top surface of valve 12. In an embodiment using an ATR spectrometer, the transparent element 25 can be the IRE.

As stated above, the digital signal can be transmitted from transmitter 30 to receiver 31 by any known technique in the wireless transmission art, such as transmission using carrier waves in the IR, radio, optical or microwave region of the wavelength spectrum. Infrared (IR) transmission uses an invisible portion of the spectrum slightly below the visible range. The IR transmission can be directed, which requires a direct line-of-site, or diffuse, which does not require line of sight.

Radio transmission uses the radio region on the spectrum, which is located above the visible portion of the spectrum. Suitable devices that allow digital signals to be transmitted in the FM radio region of the spectrum are made by Aeolus and Xircon. In certain embodiments, Xircon's Core Engine can be directly embedded in the electronics of transmitter 30 and receiver 31. In certain embodiments, transmitter 30 and receiver 31 can be linked to a Wi-Fi certified wireless network anywhere in the world, and GSM/CDMA, LAN and WAN connections can also be provided, using devices provided, for example, by 3Com or Nokia.

The digital signal may also be wirelessly transmitted from transmitter 30 to receiver 31 in the microwave frequencies, which are located below the visible range of the spectrum. Nokia microwave radios, for example, can provide a microwave link between transmitter 30 and receiver 31.

Optical devices, such as those based on lasers, can also be used to transmit the digital signal from transmitter 30 to receiver 31.

Once receiver 31 receives the digital signal from transmitter 30. Receiver 31, in turn, transmits the digital signal to a processing device 32 to which it is coupled, by any known method. Processing device 32 can be physically coupled to receiver 31, as illustrated in FIG. 1A such as through conventional cables, wires or data buses, in which case such transmission takes place through such physical connections. Processing device 32 can also be separate from receiver 31 and coupled thereto wirelessly, in which case such transmission from receiver 31 to processing device 32 takes place through any of the wireless methods discussed above. Upon receipt of the digital signal from receiver 31, processing device 32 can then process the digital signal as well as transmit the digital signal to peripherals, such as a display device 33 and/or storage device 34. In a network embodiment, processing device 32 can transmit the digital signal to subsequent processing devices. In the embodiment shown in FIG. 2, for example, processing device 32 can transmit the signal to a further remote device 38, which can transmit the digital signal to peripherals, such as a display device 33 and/or storage device 34.

The communication between spectrometer 20, receiver 31 and the processing device 32 in FIGS. 1A–1H (as well as with remote device 38 in FIG. 2) can also be via a wireless peer-to-peer network. In such a network, spectrometer 20 and attached transmitter 30 send the digital signal to processing device 32 and receiver 31, which can, for example, be a laptop PC equipped with wireless adapter card, via a wireless connection. From processing device 32, a user can analyze the digital signal, transform the digital signal, compare the digital signal to the data set in storage device 34 or display the digital signal on display device 33. Processing device 32 can be moved, so that communication with other spectrometers is possible without the need for extensive reconfiguration. In this embodiment, spectrometer 20 and transmitter 30 function as a client, while processing device 32 acts as a server.

A data reduction technique, such as a partial least squares, a principal component regression, a neural net, a classical least squares (often abbreviated CLS, and sometimes called The K-matrix Algorithm), or a multiple linear regression analysis can then be used to generate a modeling equation from the digital signal.

In certain embodiments, processing device 32 can use various algorithms to pre-treat the spectral data prior to modeling the data via the data reduction technique. For example, a baseline correction, a normalization of the spectral data, a first derivative on the spectral data, a second derivative on the spectral data, a multiplicative scatter correction on the spectral data, a smoothing transform on the spectral data, a Savitsky-Golay first derivative, a Savitsky-Golay second derivative, a mean-centering, Kubelka-Munk transform, and/or a conversion from reflectance/transmittance to absorbance can be performed. The pre-treated data signal can be displayed to the user as a spectrograph (a graphical representation of absorption as it relates to different wavelengths). One or more of these above-mentioned treatments can be performed on the data in any order desired.

A user may select which pre-treatments and/or reduction techniques to use in transforming or modeling the data. In certain embodiments, the pre-treatments and/or reduction techniques may also be selected pursuant to a set of rules specifying which algorithms to use for a particular type of composition.

Figure 7:
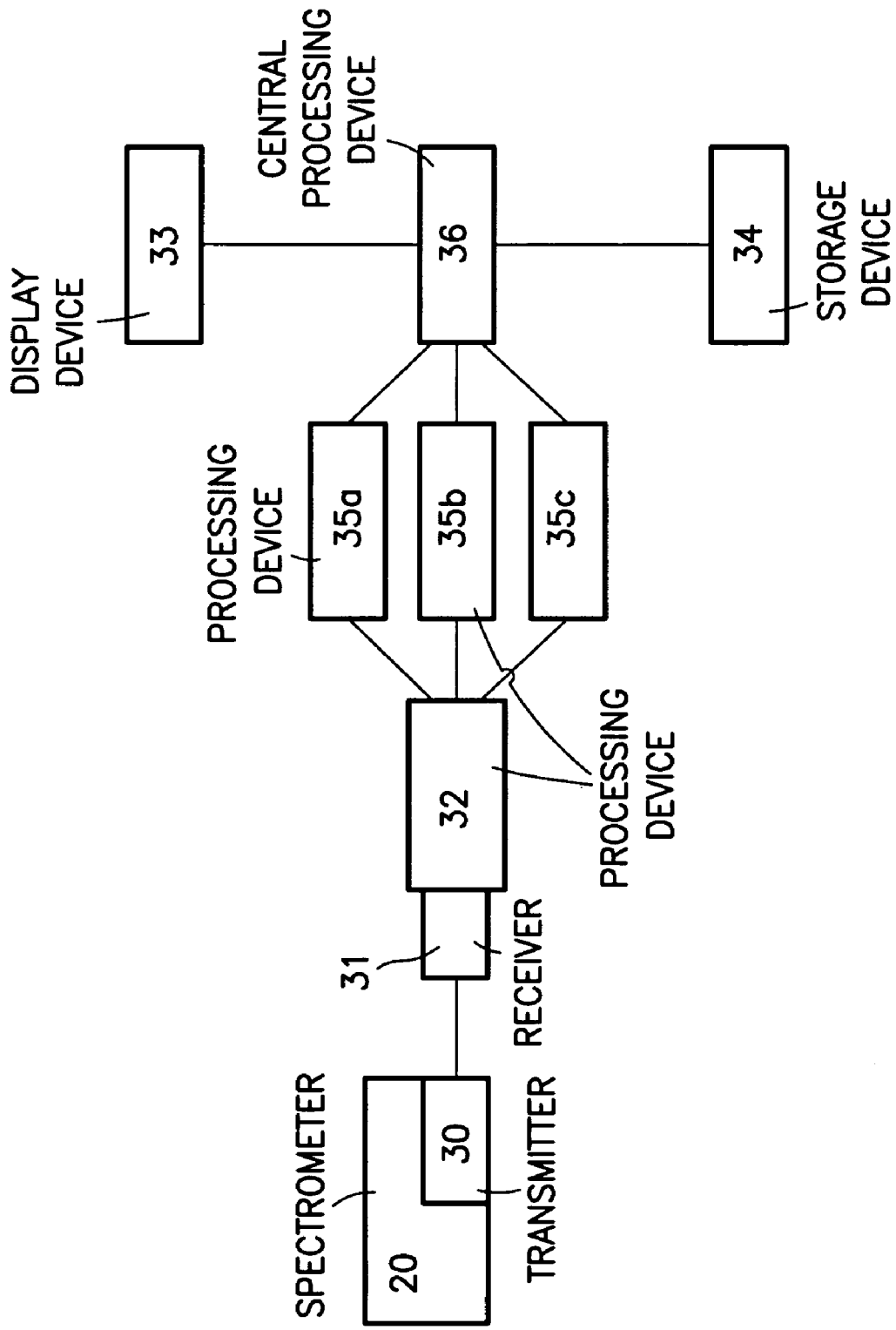
FIG. 7 shows a schematic representation of a configuration for transmitting the digital signal to a processor.

FIG. 7 shows a schematic representation of a configuration for transmitting the digital signal between spectrometer 20 and a central processing device 36, with multiple processing devices 32 and 35a, 35b, 35c arranged in a distributive network. In this configuration, spectrometer 20 includes transmitter 30 and wirelessly transmits a digital signal to receiver 31. The first processing device 32 (e.g., a routing device) receives the digital signal from receiver 31 and transmits a first portion of the digital signal to processing device 35a (e.g., a computer in a distributive network), a second portion of the digital signal to processing device 35b, and a third portion of the digital signal to processing device 35c. Processing devices 35a, 35b, 35c perform various functions on their respective portions of the digital signal in parallel (e.g., transformations of the digital signal) and then each transmits a modified digital signal to a fifth processing device 36 (e.g., a personal computer). Processing device 36 analyzes and transmits the digital signal to display device 33 (e.g., a monitor) and to storage device 34 (e.g., a hard disk). The communication between any of the devices can be via wireless communication, or the devices can be physically connected (e.g., copper wire or fiber optic cable).

Although only one spectrometer 20 with a transmitter 30 is shown in FIG. 7, an arrangement with a plurality of spectrometers, each connected to the same processing unit or distributed over the plurality of processing units, is possible. Similarly, it should be understood that the present invention is not limited to the number or configuration of processing devices 32, 35a, 35b, 35c and 36 shown in FIG. 7. Other configurations, with more or fewer processing devices, are possible.

Figure 8:
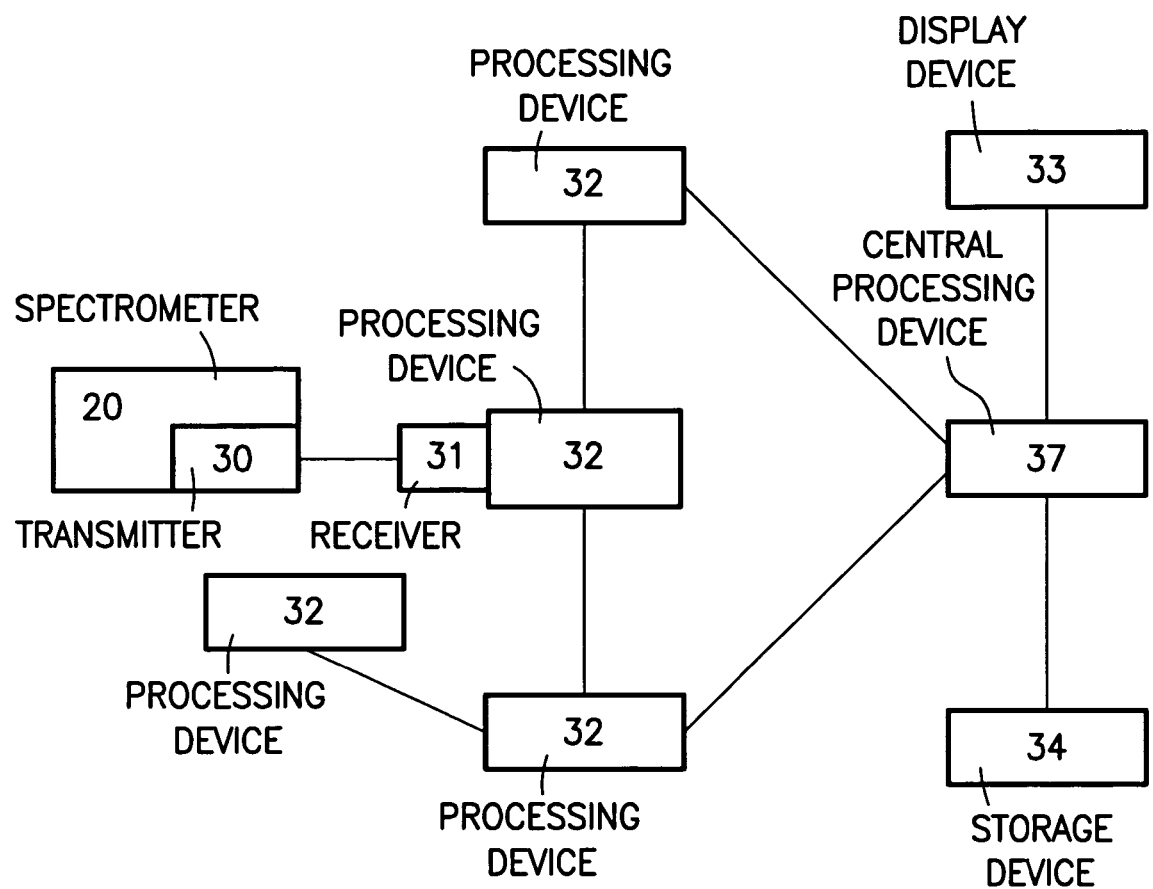
FIG. 8 shows a schematic representation of another configuration for transmitting the digital signal to a processor.

FIG. 8 shows a schematic representation of another configuration for transmitting the digital signal to a processor, between a plurality of processing devices 32 and a central processing device 37. Spectrometer 20 with associated transmitter 30 wirelessly transmits the digital signal to a receiver 31, which is integrated within or coupled to one of processing devices 32 and in communication therewith. Each processing device 32 (e.g., a routing device) transmits the digital signal either to central processing device 37 or to a different processing device 32. Central processing device 37 analyzes the digital signal. Central processing device 37 processes the digital signal and may also transmit the digital signal or selected portions of the data contained therein to display device 33 (e.g., a monitor) where it is displayed in human readable form. Central processing device 37 may also transmit the digital signal or selected portions therein to storage device 34 (e.g., a hard disk). The communication between any of the devices can be via wireless communication (e.g., radio waves). The devices can also be physically connected (e.g., by wire or fiber optic cable). Furthermore, central processing unit 37 can be mobile, such as by being mounted in a mobile platform (e.g., a laptop or hand-held device) or by itself having a mobile structure, such as a lap-top computer, so that central processing unit 37 can be placed at different positions with respect to the network. Although only one spectrometer 20 with a transmitter 30 is shown in FIG. 8, an arrangement with a plurality of spectrometers 20, each connected to the same processing unit or distributed over the plurality of processing units 32, is possible.

In certain embodiments, transmitter 30 can be a transmitter/receiver device, so that the spectrometer 20 may function with a Global Positioning System (GPS). GPS technology allows tracking of the device and may prove helpful if the spectrometer is lost or stolen. Furthermore, the GPS coordinates of hopper 10 can be sent, along with the digital signal, to a central database, so that, if a problem is detected regarding hopper 10, a repair technician could be sent directly to the hopper by using the hopper's GPS coordinates. Thus, a manufacturing plant that continues to have problems could more easily be ascertained.

Figure 9:
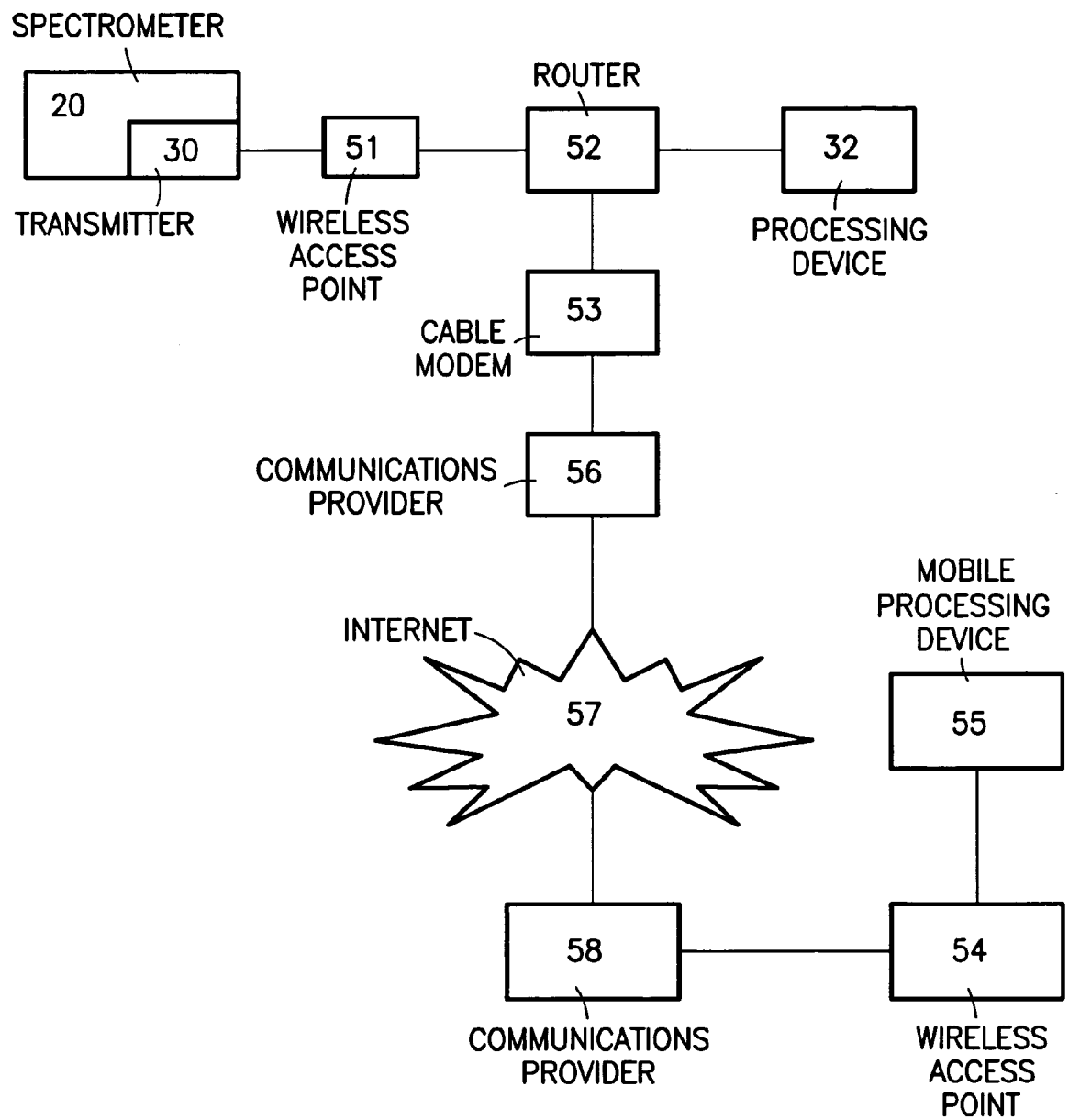
FIG. 9 shows a schematic representation of a networking arrangement for transmitting the digital signal in accordance with another embodiment of the present invention.

FIG. 9 shows a schematic representation of a networking arrangement for transmitting the digital signal in accordance with another embodiment of the present invention. The wireless access point 51 can be any suitable device, such as Linksys's WAP 11. Spectrometer 20 wirelessly transmits the digital signal to wireless access point 51 by transmitter 30. Wireless access point 51 then transmits the digital signal to a router 52 via a physical connection. Router 52 can be any suitable device, such as a Linksys' BEFSR41 4-port cable/DSL router. Router 52, in turn, transmits the data to processing device 32 and a cable modem 53. Router 52 can be connected to processing device 32 and cable modem 53 by any suitable device, such as, for example, a 10BaseT connector. At processing device 32, a user may perform functions on the data, view the data and/or store the data. Cable modem 53 transmits the digital signal over existing phone lines to a communication provider 56, e.g., AT&T, which in turn uses existing networks to transfer the digital signal to the Internet 57. From the Internet 57, the digital signal is received by another communication provider 58, e.g., America Online, which transmits the digital signal to a second wireless access point 54. Second wireless access point 54 can be any suitable device, such as a Linksys' WAP11. Provider 58 can be connected to second wireless access 54 point by, for example, existing phone lines. Second wireless access point 54 transmits the digital signal to a mobile processing device 55, such as a laptop computer, equipped with a wireless card. The wireless card can be any suitable device, such as, for example, 3Com's Wireless AirConnect PC card. From mobile processing device 55 with the wireless card or the processing device 32 a user can perform functions on the digital signal, the digital signal can be displayed and/or the digital signal can be stored.

Figure 10:
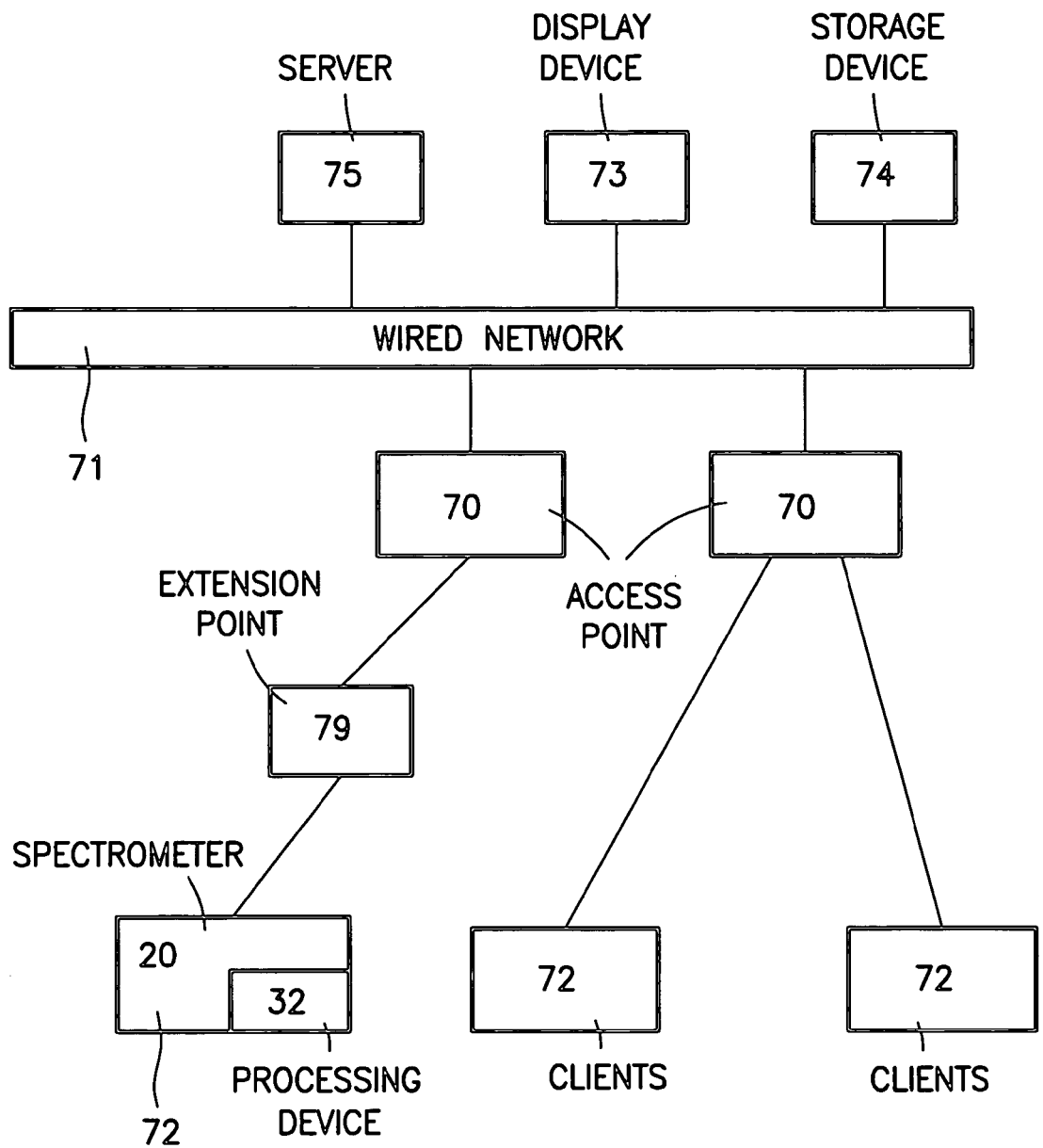
FIG. 10 shows a schematic representation of another embodiment of a networking arrangement for transmitting the digital signal.

FIG. 10 illustrates a plurality of clients 72 and a plurality of access points 70 arranged in a wireless network. In this embodiment, spectrometer 20 and transmitter 30 function as one of the clients 72. Clients 72 can also be processing device 32 (e.g., a PC or a lap-top). Each client 72 can wirelessly transmit the digital signals to a wired network 71 by transmitting to one of access points 70. Access points 70 extend the range of the wired network 71, effectively doubling the range at which the devices can communicate. Each access point 70 can accommodate one or more clients 72, the specific number of which depends upon the number and nature of the transmissions involved. For example, a single access point 70 can be configured to provide service to fifteen to fifty clients 72. In certain embodiments, clients 72 may move seamlessly (i.e., roam) among a cluster of access points. 70. In such an embodiment, access points 70 may hand client 72 off from one to another in a way that is invisible to the client 72, thereby ensuring unbroken connectivity.

Once the digital signal enters wired network 71, the digital signal can be relayed to a server 75, the display device 73 and the storage device 74, as well as to other clients 72. Server 75 or other clients 72 can convert the digital signal to a spectrograph and/or perform various algorithms on the digital signal.

In certain embodiments, an extension point 79 is provided. Extension points 79 augment the network of access points 70 and function like access points 70. However, extension points 79 are not tethered to wired network 71 as are access points 70. Instead extension points 79 communicate with one-another wirelessly, thereby extending the range of network 71 by relaying signals from a client 72 to an access point 70 or another extension point 79. Extension points 79 may be strung together in order to pass along messaging from an access point 70 to far-flung clients 72.

Figure 11:
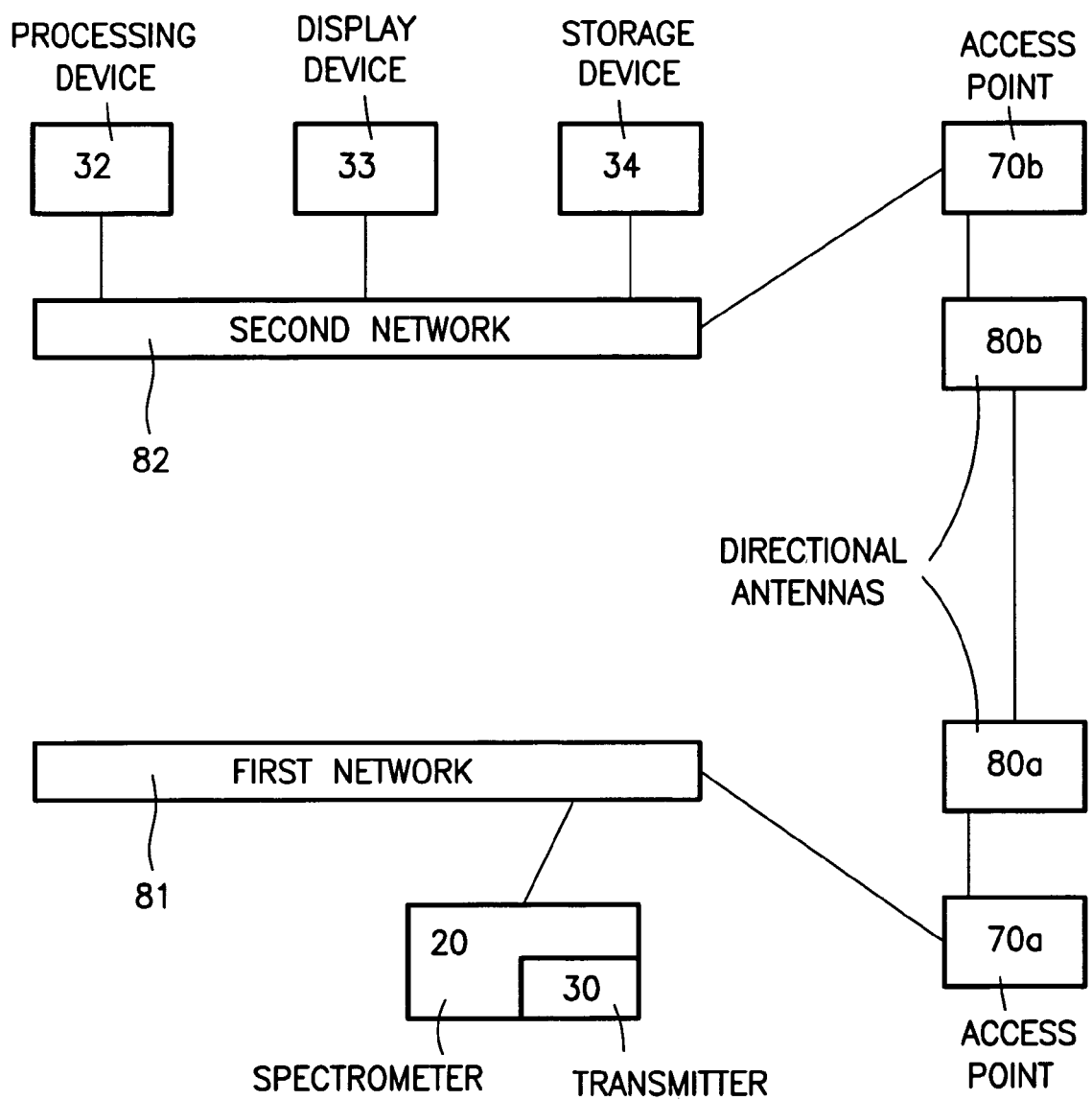
FIG. 11 shows a schematic representation of a networking arrangement for transmitting the digital signal in accordance with yet another embodiment of the present invention.

FIG. 11 shows a schematic representation of a networking arrangement for transmitting the digital signal in accordance with yet another embodiment of the present invention. Communication between first and second networks 81,82 is by directional antennas 80*a*,80*b*. Each antenna 80*a*,80*b* targets the other to allow communication between networks 81,82. First antenna 80*a* is connected to first network 81 via an access point 70*a*. Likewise, the second antenna 80*b* is connected to second network 82 by an access point 70*b*. The digital signal from spectrometer 20 is transmitted by transmitter 30 to first network 81 and is then transmitted to the directional antenna 80*a* by being relayed over the nodes of first network 81. The digital signal can then be transmitted to second directional antenna 80*b* on second network 82. Second network 82 then relays the digital signal to processing device 32, display device 33 and/or the storage device 34.

Figure 12:
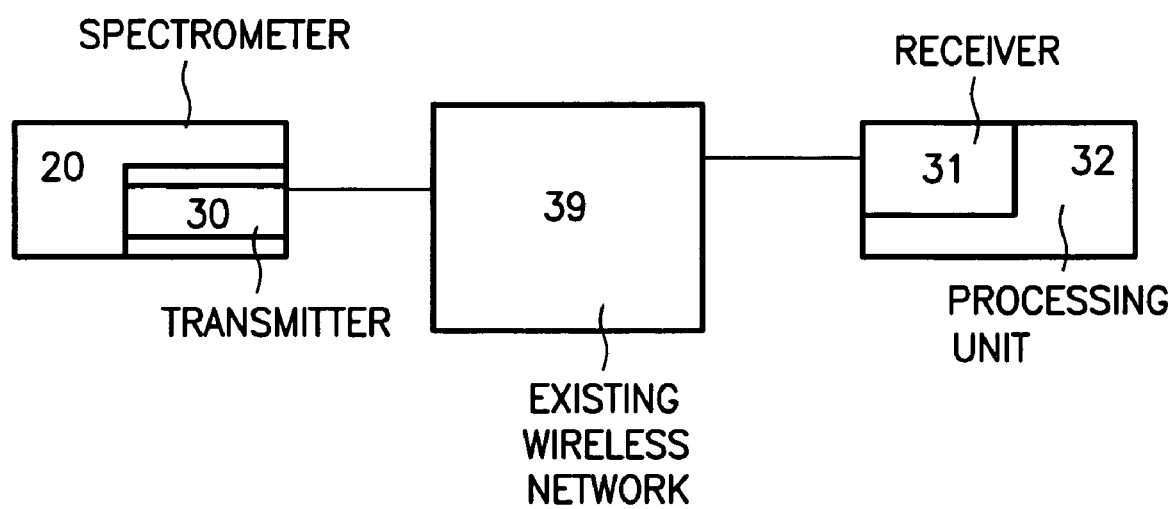
FIG. 12 shows a schematic representation of still another networking arrangement for transmitting the digital signal.

FIG. 12 shows the communication between spectrometer 20 and processing unit 32 via an existing wireless network 39. The data from spectrometer 20 is fed into a transmitter 30 located in or attached to spectrometer 20. Transmitter 30 can be, for example, the type of transmission device used in a conventional cell phone. Transmitter 30 then connects to the processing device 32 equipped with a receiver 31 (e.g., a receiver used in current cell phone technology) by opening a communication channel specific to the processing device 32 on wireless network 39 (e.g., dialing a cell phone number). Once the communication channel is established, the digital signal is then transferred to processing device 32 by routing the digital signal through the existing wireless network 39. Processing device 32 can then be connected to another network or a display device and/or storage device. Wireless network 39 can be any suitable network, such as, for example, SkyTel or Nokia's communication network. In certain embodiments, wireless network 39 can be included as part of a wireless LAN, wireless WAN, cellular/PCS network (e.g., by using a transceiver equipped with a CPDP modem), digital phone network, proprietary packet switched data network, One-way Pager, a Two-way Pager, satellite, Wireless local loop, Local Multi-point Distribution Service, Personal Area Network, and/or free space optical networks.

Figure 13:
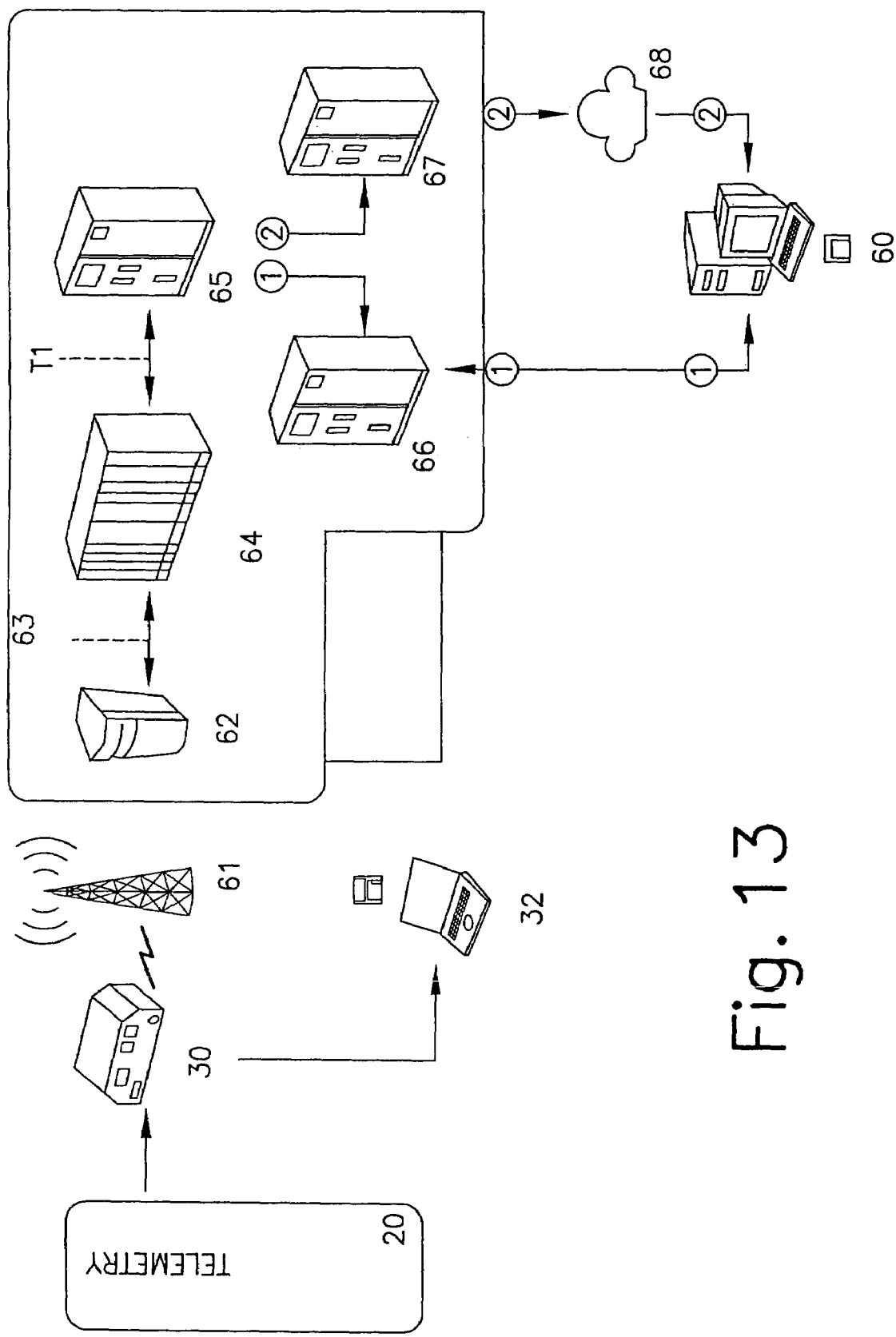
FIG. 13 shows a schematic representation of a further networking arrangement for transmitting the digital signal.

FIG. 13 shows the communication between the spectrometer 20 and an application server 60 via a wireless network. Spectrometer 20 sends the digital signal to transmitter 30, which can be, for example, Xircon's Redhawk II™. Transmitter 30 then wirelessly sends the digital signal to processing device 32, which can be, for example, a laptop computer, and to a long range transmission device 61, which transmits the digital signal to a base transceiver station 62 via a modulated radio wave. Then, through a T1 line 63, the digital signal is transmitted to a base station controller 64, which in turn transmits the digital signal to a mobile switching center 65. Based on a pre-defined user setting, mobile switching center 65 transmits the digital signal to either an interworking function device 66 or a short message center 67. If the digital signal is sent to interworking function device 66, interworking function device 66 then transmits the digital signal to an application server 60. However, if the digital signal is sent to short message center 67, short message center 67 routes the digital signal over the Internet 68 and on to the application server 60. Application server 60 provides for display of the digital signal, transfer of the digital signal to a client of server 60, analysis of the digital signal, and/or storage of the digital signal. Application server 60 can be any suitable device, such as, for example, an IBM compatible Gateway PC.

It should be apparent that the FIGS. 1–13 show merely exemplary embodiments, and other embodiments will be apparent to one skilled in the art.

FIGS. 14A–B show an illustrative remote spectrometer for performing spectral scans. As illustrated in FIG. 14A, a multiple wavelength photometer has light source 21 that produces a light beam that is focused and directed onto granulation 6 by focusing optics 25. The light that is transmitted through granulation 6 is passed through a linear variable filter 120 to an array detector 121 in order to filter and receive a number of specific, predetermined narrow bands of wavelengths simultaneously. Linear variable filters are well known in the art and are described in, for example, U.S. Pat. No. 6,057,925 to Anthon, U.S. Pat. No. 5,166,755 to Gat and U.S. Pat. No. 5,218,473 to Seddon et al., and are shown schematically in FIG. 14B. Focusing optics 25 can form a portion of wall 11 of hopper 10. In other embodiments, focusing optics 25 can be located outside hopper 10, in which case the light beam passes through window 16 in hopper 10 after impinging on focusing optics 25. Likewise, linear variable filter 120 and array detector 121 may form a portion of wall 11 of hopper 10. In other embodiments, linear variable filter 120 and array detector 121 can be located outside hopper 10, in which case the light beam passes through a second window in hopper 10 and then impinges on linear variable filter 120. Most preferably, linear variable filter 120 and array detector 121 may be used and positioned very much in the same way as focusing optics 25 and detector 26 are used and positioned in the embodiments and versions discussed elsewhere herein, such as those shown in FIGS. 1A–1F and FIGS. 2–3 and 6.

Figure 15A:
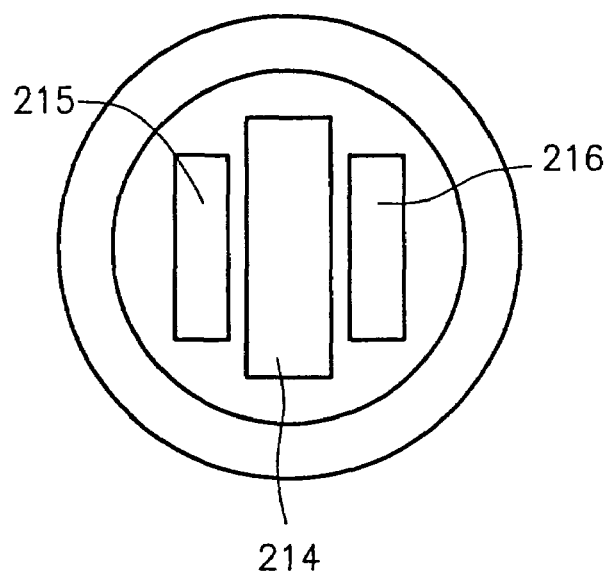
FIGS. 15A–B illustrate spectroscopic detector arrangements.
Figure 15B:
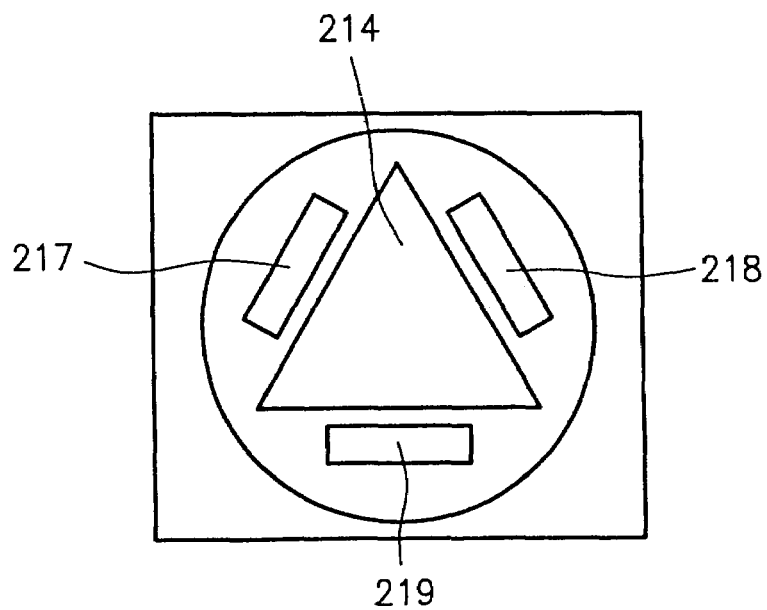

FIGS. 15A and 15B illustrate spectroscopic detector arrangements. As shown in FIG. 15A, the device includes a light emitting portion 214 and two detectors 215, 216 that surround light emitting portion 214 and can be embedded in the wall of hopper 10. Light emitting portion 214 has a light source that could be any light source, such as a quartz halogen lamp with integrated focusing optics or a fiber optic bundle, and light emitting portion 214 preferably has a rectangular prism SiO$_2$ light guide. At predetermined intervals, light emitting portion 214 emits light onto granulation 6. Detectors 215,216 then detect the light reflected off granulation 6. Detectors 215,216 are preferably formed of silicon and are preferably designed to detect only a specific range of wavelengths. For example, detector 215 could be set to detect light at wavelengths of only 400–700 nm, and detector 216 could be set to detect light at wavelengths of only 600–1100 nm. As such, the device shown in FIG. 15A would be able to detect light wavelengths of 400–1100 nm.

In one embodiment, detectors 215,216 can detect light at their specific wavelength ranges due to the presence above each filter 215,216 of an optical filter that restricts the transmission of light to detectors 215,216 at wavelengths in only the respective specified ranges.

In another embodiment, detectors 215,216 are array detectors and can detect light at their specific wavelength ranges due to the presence above each detector 215,216 of a linear variable filter 120, as shown in FIGS. 14A–B, that restricts the transmission of light to detectors 215,216 at wavelengths in only the specified, predetermined narrow band of wavelengths.

In a further preferred embodiment of a remote spectrometer, as shown in FIG. 15B, the device includes a light emitting portion 214 and three detectors 217,218,219 that surround light emitting portion 214. Light emitting portion 214 has a light source that could be any light source but is preferably a quartz halogen lamp with integrated focusing optics, and light emitting portion 214 preferably has a triangular prism SiO$_2$ light guide. At predetermined intervals light emitting portion 214 emits light onto granulation 6. Detectors 217-219 then detect the light reflected off granulation 6. The spectrometer of FIG. 15B is similar to the spectrometer of FIG. 15A, except that light emitting portion 214 is located among three detectors, rather than two detectors in FIG. 15A.

Detectors 217–219 are designed to detect only specific bands of wavelengths. For example, detectors 217–219 are preferably formed of silicon, with detector 217 detecting light at wavelengths of 400–700 nm, and detector 218 detecting light at wavelengths of 600–1100 nm. In addition, detector 219 is preferably formed of indium/gallium/arsenic (InGaAs) and detects light at wavelengths of 11–1900 nm. As such, the device can detect light wavelengths of 400–1900 nm. In one embodiment, detectors 217–219 can detect light at their specific wavelength ranges due to the presence above each detector 217–219 of an optical filter that restricts the transmission of light to detectors 217–219 at wavelengths in only the specified ranges. In another embodiment, detectors 217–219 are array detectors and can detect light at their specific wavelength ranges due to the presence above each detector 217–219 of a linear variable filter 120, as shown in FIGS. 14A–B, that restricts the transmission of light to detectors 217–219 at wavelengths in only the specified, predetermined narrow band of wavelengths.

Most preferably, the embodiments of FIGS. 15A–B may be used and positioned very much in the same way as filter 23 and detector 26 are used and positioned in the embodiments and versions discussed elsewhere herein, such as those shown in FIGS. 1A–1F and FIGS. 2–3 and 6.

Figure 16:
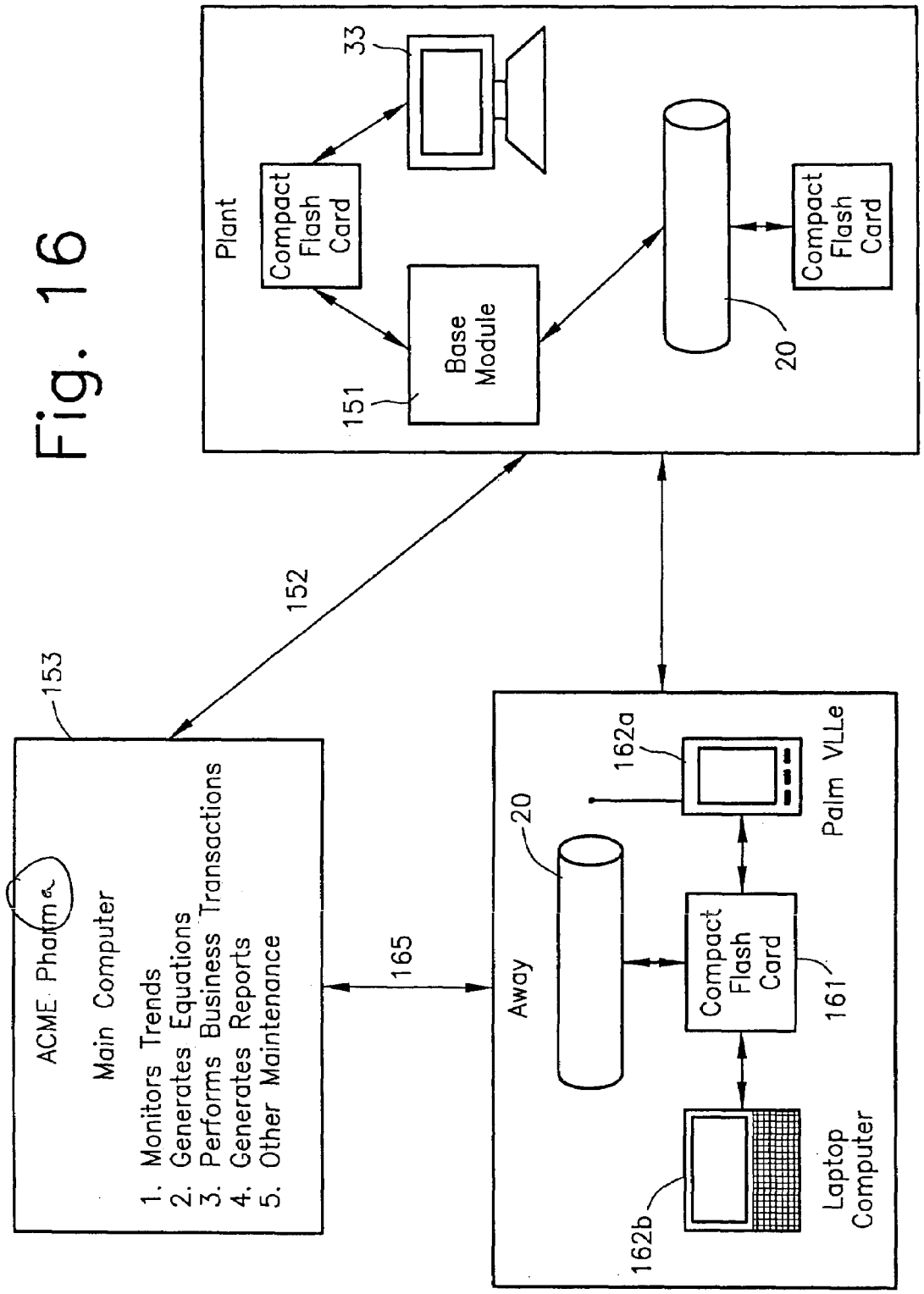
FIG. 16 illustrates the manner in which a remote wireless spectrometer can interact with a central computer.

FIG. 16 illustrates the manner in which a remote wireless spectrometer can interact with a central computer. The present invention, which can be made in accordance with any of the possible embodiments described above, is generally considered to be situated at a pharmaceutical manufacturing plant. The spectrometer 20 is connected, either directly or wirelessly, to a base module 151 that could also be situated at the pharmaceutical manufacturing plant.

In certain preferred embodiments, a further remote communication link 152 is provided between home base computer 151 and a central or main computer 153. This link 152 could be by wireless satellite cable, LAN, telephone link or any other suitable wireless connection, and could be directly from home base computer 151 to main computer 153. Main computer 153 receives and stores the spectral scan from the present invention. Main computer 153 may also monitor the purity of the granulation, including moisture changes in the granulation's profile as well as trends therein, performs analysis thereof, generates and regenerates the a modeling equation for each sample as necessary, generates reports, and performs business transactions and other tasks.

Figure 17:
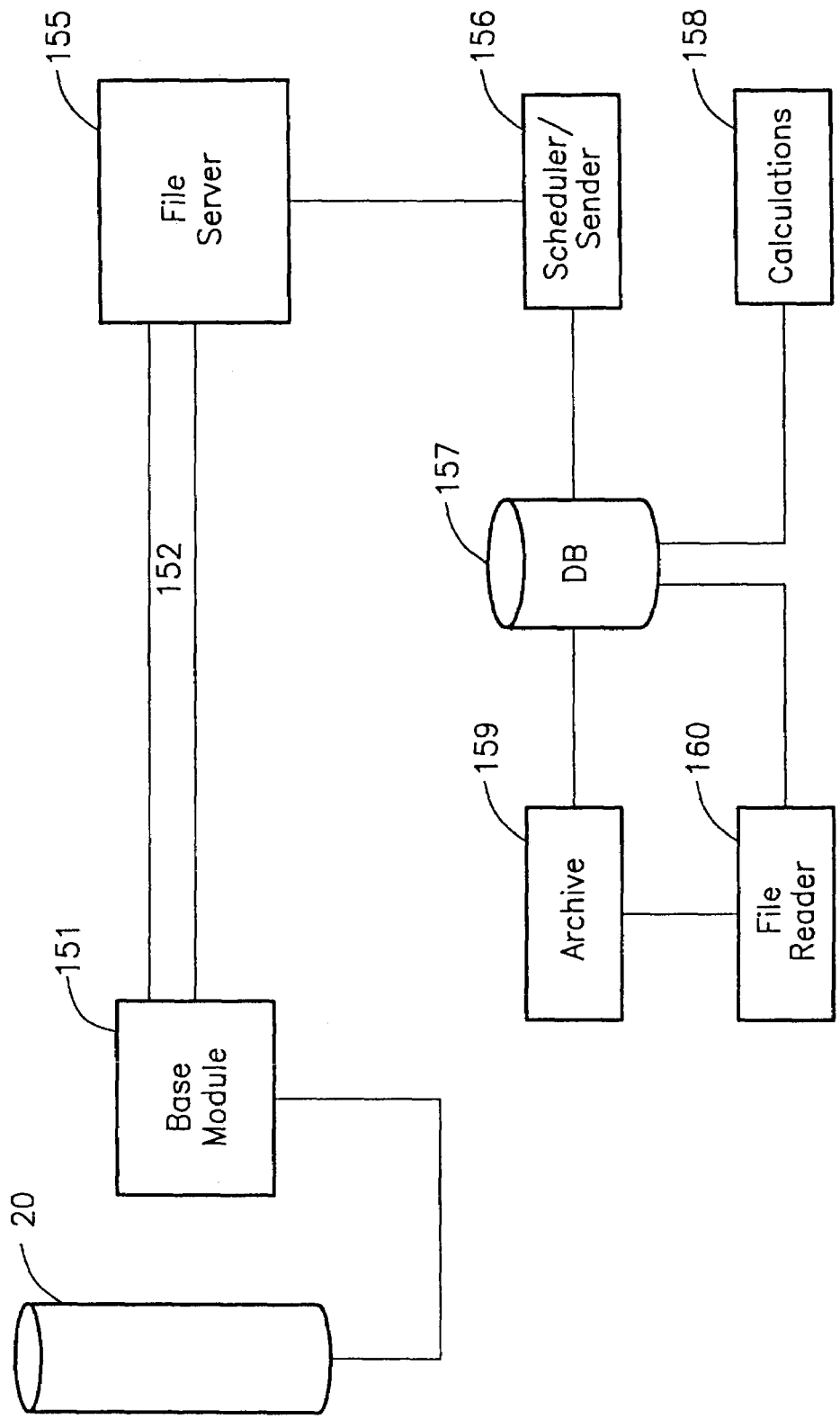
FIG. 17 illustrates in more particular detail the elements of a base connection to the main computer.

FIG. 17 shows in more particular detail the elements of a base connection to the main computer. Spectrometer 20 is connected, either directly or wirelessly, such as via a RS-232 Blue Tooth® (Wireless link, to a base module 151. The remote communication link 152 between home base computer 151 and main computer 153 can be additionally by existing dedicated telephone line, such as by dial-up modem, by wireless communication such as satellite cable, LAN, by internet, such as by cable or DSL, or even through a virtual private network (VPN) or any other suitable wireless connection. Main computer 153 preferably comprises a file server 155 that is linked to a database 157 through a scheduler/sender 156. Database 157 is also linked to calculations 158, archive 159 and file reader 160 modules.

Referring again to FIG. 16, in certain circumstances, spectrometer 20 of the present invention can be detached from hopper 10 and transported and attached to another hopper 10. Such a device could obtain the spectrographic data from a variety of different locations. Modeling equations and results can be stored in a compact flash card 161 that is attached to spectrometer 20. Spectrometer 20 can be connected, either directly or wirelessly, to a portable base module 162, such as a PALM® device 162a or a laptop computer 162b, that typically comprises a processing unit and a display device. Portable base module 162 could also be wirelessly linked to home base computer 152 for downloading and compilation of data. Portable base module 162 could also be wirelessly linked 165 to main computer 153. As discussed previously, these links 165 could be by wireless satellite cable, LAN, telephone link or any other suitable wireless connection.

Figure 18B:
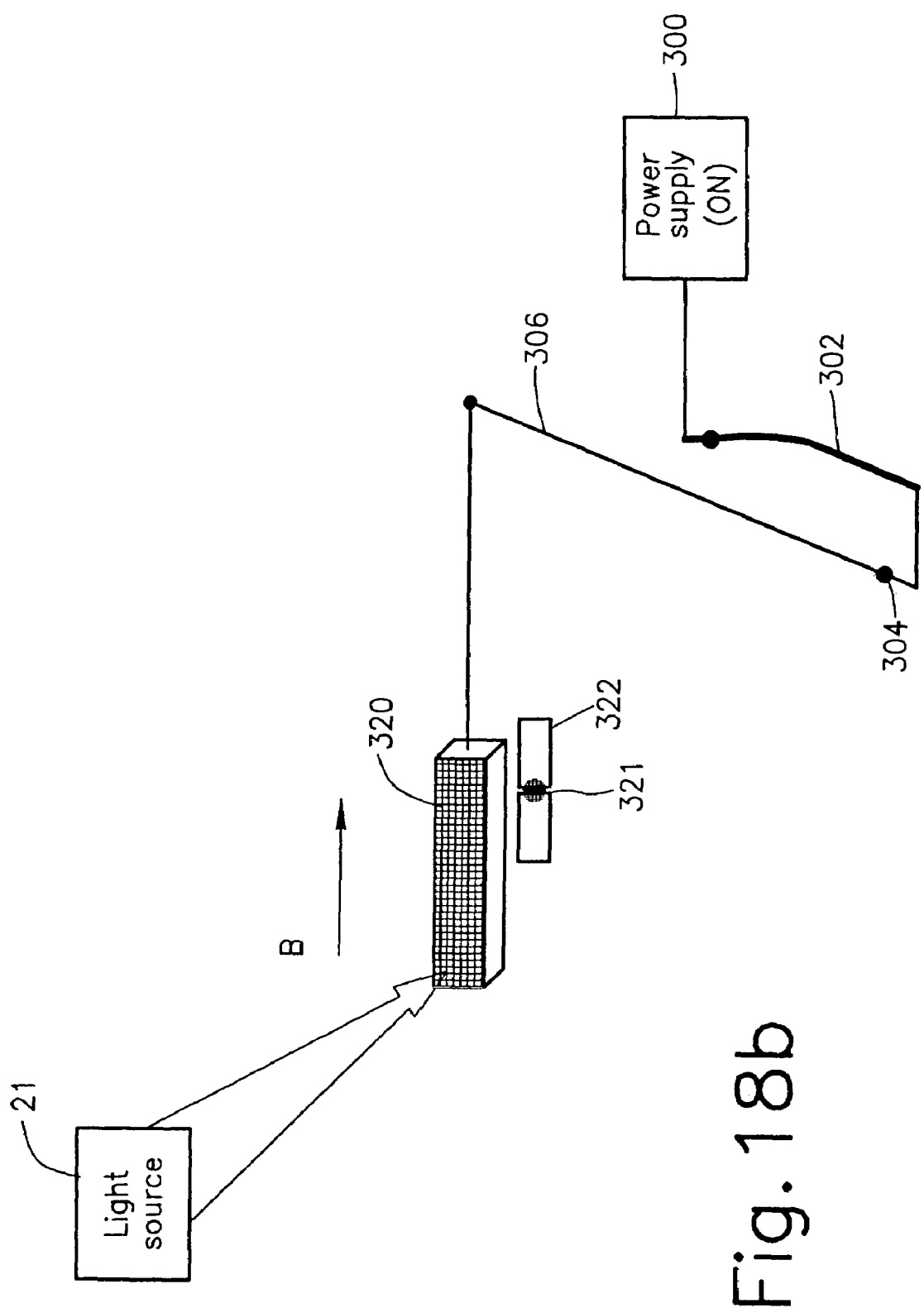

FIGS. 18A–B show a preferred embodiment of a remote spectrometer 20. As illustrated in FIG. 18A, light source 21 produces a light beam that is passed through granulation 6, through linear variable filter 320, through slit aperture 322 and onto single diode detector 321. As in the embodiments described above with reference to FIGS. 1A–F, the light from light source 21 may pass through near infrared or infrared window/transparent element 25. For example, spectrometer 20 can be set within the window 16 in the hopper 10 wall. After being transmitted through granulation 6 (as shown in FIG. 18E), or reflected off of granulation 6 (as shown in FIG. 18F), the light is passed through linear variable filter 320 (possibly via a detector imaging optic), in order in order to filter the light to a desired band of wavelengths. The light is then detected by single diode detector 321, either as transmittance or reflectance. In one embodiment, linear variable filter 320 can be arranged as a single range filter, and detector 321 is a single range detector.

The embodiment shown in FIGS. 18A–B is a scanning module because the device is equipped with piezoelectric bimorph (bender) 302 for moving linear variable filter 320 in various directions in order to allow the operator to obtain filtered scans of granulation 6 at a number of specific, predetermined narrow band of wavelengths in the light. Bimorph 302, powered by power supply 300, is connected to linear variable filter 320 via fulcrum 304 and lever 306, which amplify the displacement of the bimorph. FIG. 18A shows bimorph 302 with power supply 300 off. FIG. 18B shows bimorph 302 with power supply 300 on. With power supply 300 on, bimorph 302 bends as shown in FIG. 18B, forcing the lower portion of lever 306 to pivot about fulcrum 304 in the direction of arrow A. The pivoting of lever 306 causes linear variable filter 320 to move in the direction of arrow B, as indicated. To select each desired wavelength, power supply 300 may be controlled so as to provide predetermined power levels to bimorph 302 and thereby translate linear variable filter 320 to a desired position.

Figure 18C:
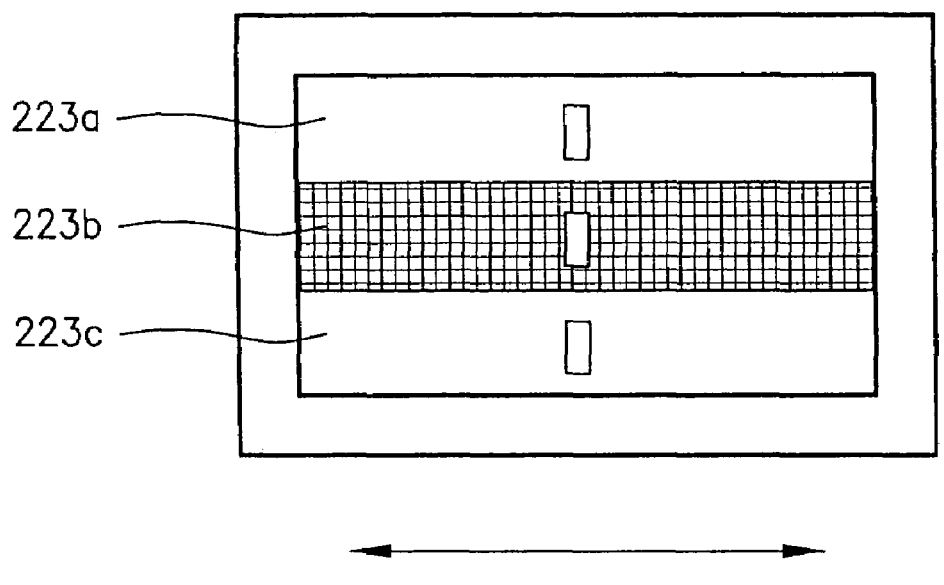
Figure 18D:
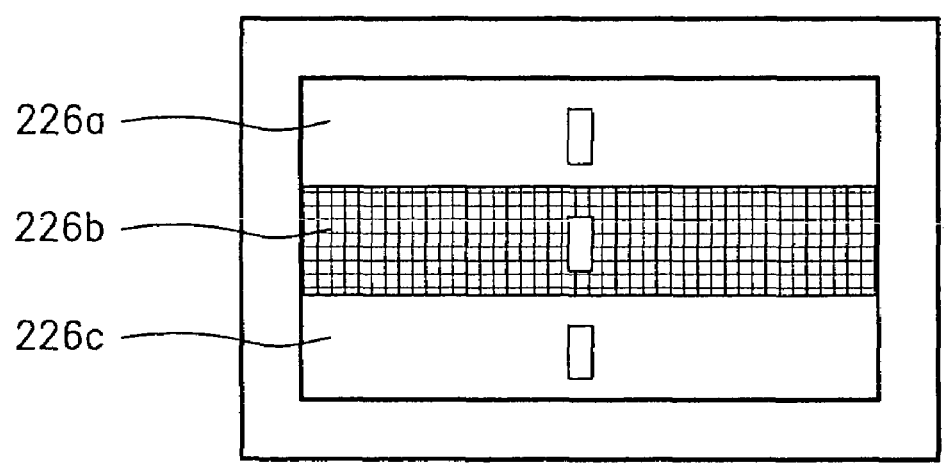
Figure 18E:
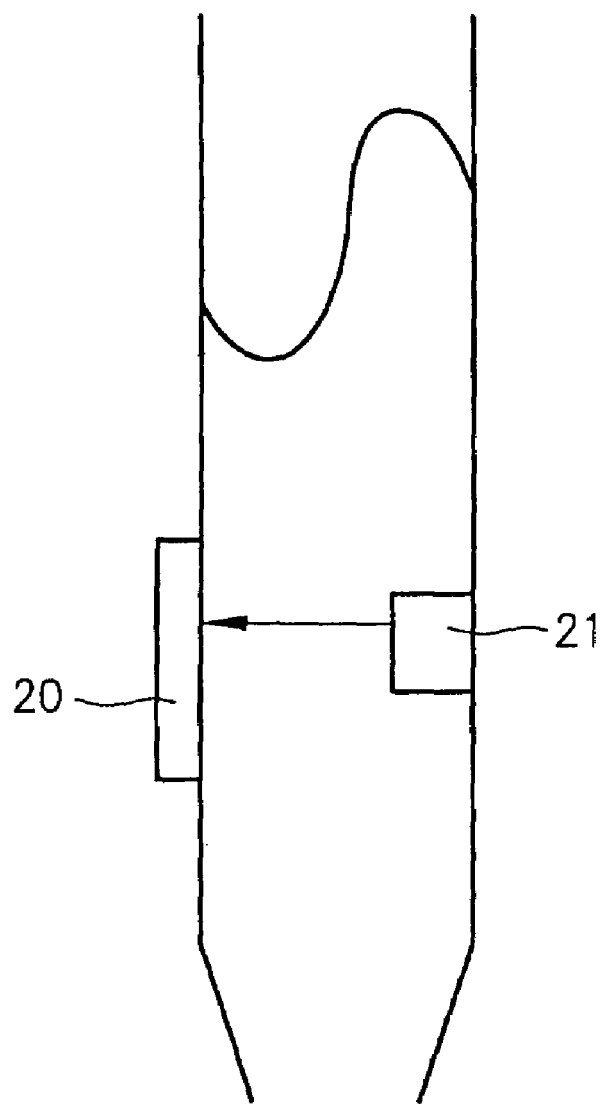
Figure 18F:
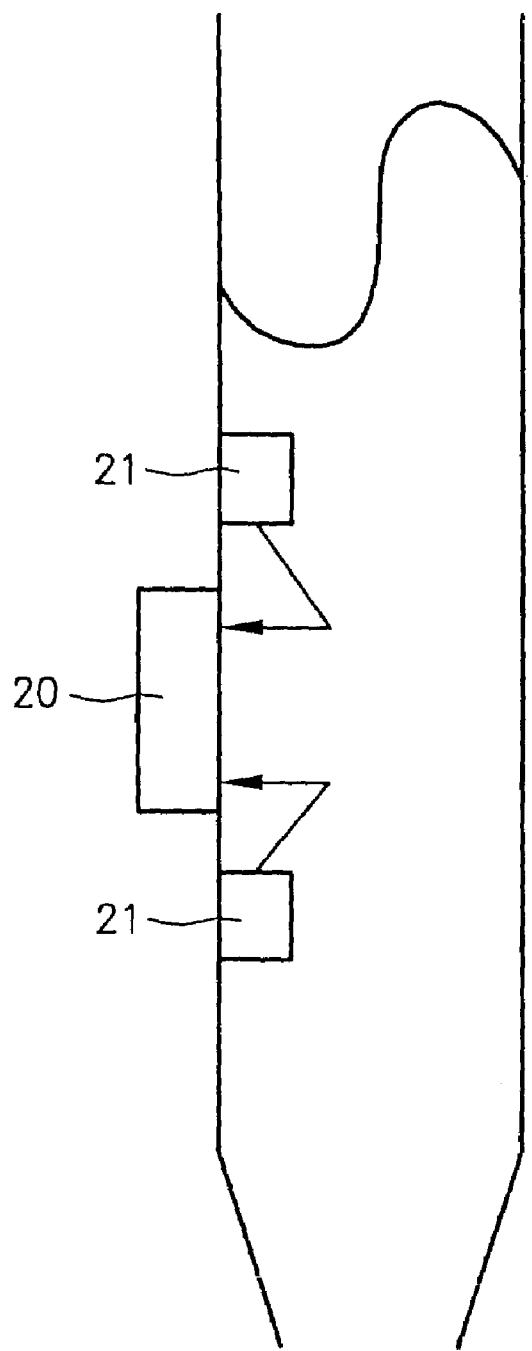

In another embodiment, linear variable filter 320 comprises separate multi-range filters 223a,223b,223c, as shown in top view in FIG. 18c. In this embodiment, each of linear variable filters 223a,223b,223c restricts the transmission of light to wavelengths in only certain specified, predetermined narrow band of wavelengths. For example, linear variable filter 223a transmits light at wavelengths of 400–700 nm, linear variable filter 223b transmits light at wavelengths of 600–1100 nm, and linear variable filter 223c transmits light at wavelengths of 1100–1900 nm. The separate multi-range linear variable filters 223a, 223b, 223c maybe moved by respective piezoelectric bimorphs. When separate multi-range filters 223a,223b,223c are used, separate detectors may also be used to detect light at only those specific bands of wavelengths. For example, as shown in top view in FIG. 1SD, detector 321 is comprised of separate detectors 226a, 226b,226c such that detector 226a detects light at wavelengths of 400–700 nm, detector 226b detects light at wavelengths of 600–1100 nm, and detector 226c detects light at wavelengths of 1100–1900 nm. As such, the device can detect light wavelengths of 400–1900 nm.

The operation of this device will be shown with regard to the multi-range filter and detector embodiment but applies equally to the single range filter and detector embodiment. The operator programs the processing device (not shown) as to the desired wavelengths or ranges of wavelengths to be scanned, and the piezoelectric bimorphs move linear variable filters 223a,223b,223c so as to allow only the desired wavelengths to pass. Thus, the light 21 is filtered to the desired band of wavelengths by linear variable filters 223a, 223b,223c is focused onto array detectors 226a,226b,226c, through detector imaging optic 225 (or one for each of detectors 226a,226b,226c), which detect light at the specific wavelength ranges.

Alternatively, the operator may operate the device manually so as to allow scans to be taken at only the particular wavelengths specified at the time by the operator.

The embodiment of the invention shown in FIGS. 19A–B is "solid state" in the sense that no electric motor is used to move linear variable filter 320. Piezoelectric bimorph 302 may be capable of very precise and repeatable positioning to within fractions of a micron, allowing for advantageous wavelength reproducibility. Linear variable filter 320 may be, for example, 2–3 mm in length, thereby enabling a relatively small overall size of spectrometer 20. Spectrometer 20 may be used in a wavelength range from ultraviolet to the mid infrared (200 nm–10,000 nm) by selecting the appropriate combination of linear variable filter 320 and single diode detector 321.

Thus, an apparatus for analyzing for monitoring homogeneity and detecting stratification of a granulation of pharmaceutical components as they are being prepared in a dosage form has been disclosed. One skilled in the art will appreciate that the present invention can be carried out in other ways and practiced by other than the described embodiments. The present embodiments therefore should be considered in all respects as illustrative, and the present invention is limited only by the claims that follow.

What is claimed is:

1. An apparatus for detecting a spectroscopic characteristic of a pharmaceutical mixture, the apparatus comprising:
   a hopper for containing a mixture of two or more pharmaceutical components;
   a spectrometer mounted to said hopper, the spectrometer measuring a spectroscopic characteristic of the contents of said hopper, the spectrometer having associated therewith a transmitter, the transmitter operable to wirelessly transmit information indicative of the spectroscopic characteristic; and
   a processing device not physically coupled to said spectrometer and not physically coupled to said transmitter, said processing device wirelessly receiving the information from the transmitter and being operable to determine a moisture content of the mixture from the information.

2. The apparatus of claim 1, wherein said processing device is remote from said spectrometer.

3. The apparatus of claim 1, wherein said processing device is remote from said transmitter.

4. The apparatus of claim 1, wherein the processing device is operable to determine a homogeneity of the mixture from the information.

5. The apparatus according to claim 1, wherein the apparatus includes a plurality of spectrometers mounted to said hopper, each spectrometer having associated therewith a transmitter operable to wirelessly transmit information indicative of the spectroscopic characteristic, and wherein the processing device wirelessly receives information from each of the transmitters.

6. The apparatus according to claim 5,
   wherein the hopper includes an input for receiving the mixture, and output for dispensing the mixture, and wherein the mixture follows a transmission path between the input and the output, and
   wherein the spectrometers are spaced apart along the transmission path.

7. The apparatus according to claim 5,
   wherein the hopper includes an input for receiving the mixture, and output for dispensing the mixture, and wherein the mixture follows a transmission path between the input and the output, and
   wherein the spectrometers are spaced apart along a plane perpendicular to the transmission path.

8. An apparatus for detecting the homogeneity of a pharmaceutical mixture, the apparatus comprising:
   a hopper for containing a mixture of two or more pharmaceutical components, said hopper being situated within a production line of preparation of a pharmaceutical dosage form from said mixture;
   a spectrometer mounted to said hopper, said spectrometer comprising a light source including a fiber optic bundle for irradiating said contents of said hopper and illuminating a plurality of positions in a neck region of said hopper and further comprising at least one detector for detecting radiation reflected off or transmitted through said mixture, the spectrometer measuring spectroscopic characteristics of the contents of said hopper;
   a processing device not physically coupled to said spectrometer, said processing device being adapted to analyze information regarding said spectroscopic characteristics of said hopper contents and derive therefrom information regarding the homogeneity of said mixture of pharmaceutical components;
   a plurality of optical fibers spaced apart on the neck for receiving radiation reflected off or transmitted through said mixture and delivering said respective radiation to said at least one detector; and
   a switching device coupled to each of the plurality of optical fibers and to the at least one detector, the switching device configured to connect one of said respective optical fiber at a time to said at least one detector;
   wherein said spectrometer measures spectroscopic characteristics of the contents of said hopper and wirelessly sends information regarding said spectroscopic characteristics to said processing device, and said processing device derives, from said spectroscopic information, information regarding the homogeneity of said mixture of pharmaceutical components.

9. The apparatus of claim 8, wherein said processing device is remote from said spectrometer.

10. The apparatus of claim 8, wherein said device for measuring spectroscopic characteristics comprises a transmitter coupled thereto for wirelessly sending said information regarding said spectroscopic characteristics, and wherein said processing device is remote from said transmitter.

11. The apparatus of claim 8, wherein said device for measuring spectroscopic characteristics comprises a transmitter coupled thereto for wirelessly sending said information regarding said spectroscopic characteristics, and wherein said processing device comprises a receiver coupled thereto for wirelessly receiving said information regarding said spectroscopic characteristics.

12. The apparatus of claim 11, wherein said information regarding said spectroscopic characteristics is converted to digital signals prior to being wirelessly sent to said processing device.

13. The apparatus of claim 11, further comprising a display device coupled to said processing device for display of said information regarding the homogeneity of said mixture of pharmaceutical components.

14. The apparatus of claim 8, wherein said hopper comprises an aperture, and wherein said measuring device is mounted to said hopper adjacent said aperture.

15. The apparatus of claim 8, wherein at least one of said plurality of optical fibers associated with said at least one detector is on a side of said hopper proximate to at least one of said optic fibers associated with said light source for detecting light reflected off said mixture.

16. The apparatus of claim 8, wherein at least one of said plurality of optical fibers associated with said at least one detector is on a side of said hopper remote from at least one of said optic fibers associated with said light source for detecting light transmitted through said mixture.

17. The apparatus of claim 8, wherein said light source emits radiation in multiple wavelengths, said apparatus further comprising a filter for restricting passage of light through said filter in only a specific predetermined range of wavelengths.

18. The apparatus of claim 17, wherein said filter is situated between said light source and said mixture, such that said filter allows passage of light in only a specific predetermined range of wavelengths to pass to said mixture.

19. The apparatus of claim 17, wherein said filter is situated between said mixture and said at least one detector, such that said filter allows passage of only a specific predetermined range of wavelengths reflected off or transmitted through said mixture to pass to said at least one detector.

20. The apparatus of claim 17, wherein said filter is at least one linear variable filter.

21. The apparatus of claim 20, further comprising a solid state translation device operatively connected to said at least one linear variable filter and configured for moving said at least one linear variable filter.

22. The apparatus of claim 21, wherein said at least one detector comprises a plurality of detectors.

23. The apparatus of claim 21, wherein said solid state translation device is a piezoelectric bimorph.

24. The apparatus of claim 23, further comprising a lever device coupling said piezoelectric bimorph to said at least one linear variable filter and configured for amplifying a movement of said at least one linear variable filter relative to a movement of said piezoelectric bimorph.

25. The apparatus of claim 20, wherein said detector is at least one array detector.

26. The apparatus of claim 20, wherein said detector is at least one diode.

27. The apparatus of claim 17, wherein the filter is a bandpass filter.

28. The apparatus of claim 27, wherein the filter includes a plurality of bandpass filters.

29. The apparatus of claim 17, wherein said filter is a grating.

30. The apparatus of claim 29, wherein said grating is a diffraction grating.

31. The apparatus of claim 8, wherein said light source emits light in only a specific predetermined range of wavelengths, and wherein said at least one detector detects light reflected off or transmitted through said mixture in said specific predetermined range of wavelengths.

32. The apparatus of claim 8, wherein said light source emits light in multiple wavelengths, and wherein each of said at least one detector detects light reflected off or transmitted through said mixture in only a specific predetermined range of wavelengths.

33. The apparatus of claim 8, wherein said measuring device sends information regarding said spectroscopic characteristics to said processing device through infrared radiation or near infrared radiation.

34. An apparatus for determining spectroscopic characteristics of one or more components, comprising:
a hopper for adding one or more components to a tableting/encapsulation machine, the hopper having an aperture fitted with a window, one side of the window forming a portion of an interior surface of the hopper;
a light source for transmitting a beam of light, the beam impinging the window, and then a detector, the detector optically connected to the beam of light and converting the beam of light into a digital signal;
a transmitter for receiving the digital signal from the detector and sending the digital signal to a processor via a wireless link; and
a processor for analyzing a spectroscopic characteristic of the one or more components based on the digital signal, wherein the spectroscopic characteristic is indicative of a moisture content of the one or more components.

35. The apparatus of claim 34, wherein said transmitter is coupled to said processor, the transmitter receiving the profile from the processor and transmitting the spectroscopic characteristics as a second digital signal to a receiver via a wireless link.

36. The apparatus of claim 34, wherein the one or more components form a mixture, and wherein the spectroscopic characteristic is indicative of the homogeneity of the mixture.

37. A method for determining the homogeneity of a pharmaceutical mixture in a hopper, comprising the steps of:
feeding a mixture of at least two pharmaceutical substances into a hopper, the hopper having a window, one face of the window forming a portion of an interior surface of the hopper and the window optically connected to a light source;
projecting light from said light source onto said mixture;
receiving information from a detector that is optically connected to the window as the pharmaceutical mixture is being mixed; and
analyzing the information from the detector; and
determining the homogeneity and moisture content of the pharmaceutical mixture.

38. The apparatus of claim 8, wherein the mixture is a granulation.

39. The apparatus of claim 8, wherein the mixture is a dry blend.

40. The method of claim 37, wherein the mixture is a granulation.

41. The method of claim 37, wherein the mixture is a dry blend.

42. A method for detecting a spectroscopic characteristic of a pharmaceutical mixture in a hopper, comprising the steps of:
feeding a mixture of one or more pharmaceutical components into a hopper;
measuring a spectroscopic characteristic of the contents of said hopper with a spectrometer mounted to said hopper,
transmitting the spectroscopic characteristic to a processing device via a transmitter, the transmitter associated with the spectrometer and operable to wirelessly transmit information indicative of the spectroscopic characteristic, and
determining a moisture content of the mixture from the spectroscopic characteristic.

43. The method of claim 42 further comprising the step of receiving, via a wireless connection, the spectroscopic characteristic at a processing device, the processing device not physically coupled to said spectrometer and not physically coupled to said transmitter.

44. The method of claim 43, wherein said processing device is remote from said spectrometer.

45. The method of claim 43, wherein said processing device is remote from said transmitter.

46. The method of claim 43, further comprising the step of determining a homogeneity of the mixture from the spectroscopic characteristic.

47. The method of claim 43, wherein the spectrometer further comprises a plurality of spectrometers; and wherein the transmitter further comprises a plurality of transmitters each transmitter associated with at least on one of the spectrometers; and wherein the step of receiving further comprises receiving a plurality of spectroscopic characteristics from each of the transmitters.

48. The method of claim 47, wherein the hopper includes an input for receiving the mixture, and output for dispensing the mixture; wherein the mixture follows a transmission path between the input and the output; and wherein the spectrometers are spaced apart along the transmission path.

49. The method of claim 47, wherein the hopper includes an input for receiving the mixture, and an output for dispensing the mixture; wherein the mixture follows a transmission path between the input and the output; and wherein the spectrometers are spaced apart along a plane perpendicular to the transmission path.

50. A method for detecting a spectroscopic characteristic of a pharmaceutical mixture in a hopper, comprising the steps of:
   feeding a mixture of one or more pharmaceutical components into a hopper;
   measuring a spectroscopic characteristic of the contents of said hopper with a spectrometer mounted to said hopper,
   transmitting the spectroscopic characteristic to a processing device via a transmitter, the transmitter associated with the spectrometer and operable to wirelessly transmit information indicative of the spectroscopic characteristic, and
   pre-treating the spectroscopic characteristic with a pre-treatment technique selected from the group consisting of: a baseline correction, a normalization of the spectral data, a first derivative on the spectral data, a second derivative on the spectral data, a multiplicative scatter correction on the spectral data, a smoothing transform on the spectral data, a Savitsky-Golay first derivative, a Savitaky-Golay second derivative, a mean-centering, a Kubelka-Munk transform, and a conversion from reflectance/transmittance to absorbence.

51. A method for detecting a spectroscopic characteristic of a pharmaceutical mixture in a hopper, comprising the steps of:
   feeding a mixture of one or more pharmaceutical components into a hopper;
   measuring a spectroscopic characteristic of the contents of said hopper with a spectrometer mounted to said hopper,
   transmitting the spectroscopic characteristic to a processing device via a transmitter, the transmitter associated with the spectrometer and operable to wirelessly transmit information indicative of the spectroscopic characteristic.
   pre-treating the spectroscopic characteristic with a pre-treatment technique, and
   applying a data reduction technique to the spectroscopic characteristic.

52. The method of claim 51, wherein the data reduction technique is selected from the group consisting of: partial least squares, a neural net, a classical least squares, a principal component regression, and a multiple linear regression.

53. The method of claim 50, further comprising applying a data reduction technique to the pre-treated spectroscopic characteristic.

54. The method of claim 53, wherein the data reduction technique is selected from the group consisting of a partial least squares, a neural net, a classical least squares, a principal component regression, and a multiple linear regression.

55. The apparatus of claim 8, farther comprising a tableting press for tableting the mixture, the tableting press located downstream from the hopper and coupled to an output of the hopper.

56. The apparatus of claim 8, further comprising a mixer for mixing two or more pharmaceutical compositions, the mixer located upstream from the hopper and coupled to an input of the hopper.

57. The apparatus of claim 8, further comprising an encapsulating press for encapsulating mixture, the encapsulating press located downstream from the hopper and coupled to an output of the hopper.

58. The apparatus of claim 55, wherein the hopper is integrated into the tableting press.

59. The apparatus of claim 56, wherein the mixer is integrated into the hopper.

60. The apparatus of claim 57, wherein the hopper is integrated into the encapsulating press.

61. The apparatus of claim 8, wherein said light source includes a plurality of near-infrared light emitting diodes, each for illuminating a respective position of the plurality of positions.

62. An apparatus for detecting the homogeneity of a pharmaceutical mixture, the apparatus comprising:
   a hopper for containing a mixture of two or more pharmaceutical components, said hopper being situated within a production line of preparation of a pharmaceutical dosage form from said mixture;
   a spectrometer mounted to said hopper, said spectrometer comprising a light source including a fiber optic bundle for irradiating said contents of said hopper and illuminating a plurality of positions in a neck region of said hopper and further comprising at least one detector for detecting radiation reflected off or transmitted through said mixture, wherein said at least one detector is disposed in said neck region for detecting light reflected off or transmitted through said mixture, the spectrometer measuring spectroscopic characteristics of the contents of said hopper; and
   a processing device not physically coupled to said spectrometer, said processing device being adapted to analyze information regarding said spectroscopic characteristics of said hopper contents and derive therefrom information regarding the homogeneity of said mixture of pharmaceutical components;
   wherein said spectrometer measures spectroscopic characteristics of the contents of said hopper and wirelessly sends information regarding said spectroscopic characteristics to said processing device, and said processing device derives, from said spectroscopic information, information regarding the homogeneity of said mixture of pharmaceutical components.

63. The apparatus of claim 62, wherein each of said at least one detector is configured for detecting a respective wavelength of light.

64. The apparatus of claim 1, further comprising at least one second spectrometer and wherein said spectrometer and each of said at least one second spectrometer include a respective light source for irradiating a portion of said contents of said hopper at a respective position.

65. The apparatus of claim 64, wherein said spectrometer and each of said at least one second spectrometer are disposed at a respective position on said hopper.

66. The apparatus of claim 65, wherein each of said respective position is at a respective longitudinal level of said hopper so as to enable a determination of stratification in said mixture.

67. The apparatus of claim 64, wherein each said light source includes a respective individual optical fiber of a common fiber optic bundle light source.

68. The apparatus of claim 67, further comprising a filter device for restricting passage of light from the common fiber optic bundle light source through said filter to a predetermined wavelength or range of wavelengths.

69. The apparatus of claim 64, wherein said spectrometer and each of said at least one second spectrometer include a respective detector for detecting respective radiation reflected off or transmitted through said mixture.

70. The apparatus of claim 64, wherein each of said respective light source are disposed at a respective position in a neck region of said hopper.

71. The apparatus of claim 70, wherein each of said respective light source includes a near-infrared light emitting diode.

72. The apparatus of claim 70, further comprising a plurality of detectors disposed in said neck region for detecting light reflected off or transmitted through said mixture.

73. The apparatus of claim 72, wherein the plurality of detectors are each configured for detecting a respective wavelength of light.

74. An apparatus for detecting the homogeneity of a pharmaceutical mixture, the apparatus comprising:

a hopper for containing a mixture of two or more pharmaceutical components, said hopper being situated within a production line of preparation of a pharmaceutical dosage form from said mixture;

a spectrometer mounted to said hopper, the spectrometer measuring spectroscopic characteristics of the contents of said hopper, said spectrometer comprising a light source emitting radiation in multiple wavelengths for irradiating said contents of said hopper and at least one detector for detecting radiation reflected off or transmitted through said mixture;

at least one linear variable filter for restricting passage of light through said filter in only a specific predetermined range of wavelengths;

a solid state translation device operatively connected to said at least one liner variable filter and configured for moving said at least one linear variable filter; and a processing device not physically coupled to said spectrometer, said processing device being adapted to analyze information regarding said spectroscopic characteristics of said hopper contents and derive therefrom information regarding the homogeneity of said mixture of pharmaceutical components;

wherein said spectrometer measures spectroscopic characteristics of the contents of said hopper and wirelessly sends information regarding said spectroscopic characteristics to said processing device, and said processing device derives, from said spectroscopic information, information regarding the homogeneity of said mixture of pharmaceutical components.

75. The apparatus of claim 74, wherein said at least one detector comprises a plurality of detectors.

76. The apparatus of claim 74, wherein said solid state translation device is a piezoelectric bimorph.

77. The apparatus of claim 76, further comprising a lever device coupling said piezoelectric bimorph to said at least one linear variable filter and configured for amplifying a movement of said at least one linear variable filter relative to a movement of said piezoelectric bimorph.

* * * * *